US008435939B2

(12) United States Patent
Fujii

(10) Patent No.: US 8,435,939 B2
(45) Date of Patent: *May 7, 2013

(54) POLYPEPTIDE ANTI-HIV AGENT CONTAINING THE SAME

(75) Inventor: Nobutaka Fujii, Ohtsu (JP)

(73) Assignee: Biokine Therapeutics Ltd., Nes Ziona (IL)

( * ) Notice: Subject to any disclaimer, the term of this patent is extended or adjusted under 35 U.S.C. 154(b) by 157 days.

This patent is subject to a terminal disclaimer.

(21) Appl. No.: 12/583,746

(22) Filed: Aug. 25, 2009

(65) Prior Publication Data

US 2010/0222256 A1    Sep. 2, 2010

Related U.S. Application Data

(60) Continuation-in-part of application No. 11/497,225, filed on Aug. 1, 2006, now Pat. No. 7,595,298, which is a division of application No. 10/363,209, filed as application No. PCT/JP01/07668 on Sep. 5, 2001, now Pat. No. 7,138,488.

(30) Foreign Application Priority Data

Sep. 5, 2000   (JP) ................... 2000-269296
Mar. 28, 2001  (JP) ................... 2001-092306

(51) Int. Cl.
*A01N 37/18*     (2006.01)
*A61K 38/00*     (2006.01)
*A61P 31/12*     (2006.01)

(52) U.S. Cl.
USPC .......................................................... 514/3.7

(58) Field of Classification Search .................. None
See application file for complete search history.

(56) References Cited

U.S. PATENT DOCUMENTS

| | | | |
|---|---|---|---|
| 4,179,337 A | 12/1979 | Davis et al. | |
| 4,342,828 A | 8/1982 | Takaku et al. | |
| 5,206,018 A | 4/1993 | Sehgal et al. | |
| 5,250,732 A | 10/1993 | Kogan et al. | |
| 5,492,126 A | 2/1996 | Hennige et al. | |
| 5,595,756 A | 1/1997 | Bally et al. | |
| 6,128,522 A | 10/2000 | Acker et al. | |
| 6,365,583 B1 | 4/2002 | MacFarland et al. | |
| 6,576,875 B1 | 6/2003 | Kleffner et al. | |
| 6,875,738 B1 | 4/2005 | Clark-Lewis et al. | |
| 6,946,445 B1 | 9/2005 | Clark-Lewis et al. | |
| 7,138,488 B2* | 11/2006 | Fujii ............................. | 530/326 |
| 7,169,750 B2 | 1/2007 | Bridger et al. | |
| 7,291,631 B2 | 11/2007 | Bridger et al. | |
| 7,423,007 B2* | 9/2008 | Fujii et al. ...................... | 512/14 |
| 7,595,298 B2* | 9/2009 | Fujii ............................. | 514/1.1 |
| 7,630,750 B2 | 12/2009 | Liang et al. | |
| 8,017,585 B2* | 9/2011 | Fujii et al. ..................... | 514/21.5 |
| 2002/0156034 A1 | 10/2002 | Tudan et al. | |
| 2004/0116655 A1 | 6/2004 | Fujii | |
| 2004/0209921 A1 | 10/2004 | Bridger et al. | |
| 2005/0002939 A1 | 1/2005 | Zlotnik et al. | |
| 2005/0043367 A1 | 2/2005 | Bridger et al. | |
| 2006/0008465 A1 | 1/2006 | Steinaa et al. | |
| 2006/0079492 A1 | 4/2006 | Ahlem et al. | |
| 2006/0264378 A1 | 11/2006 | Fujii et al. | |
| 2006/0264605 A1 | 11/2006 | Fujii | |
| 2007/0129760 A1 | 6/2007 | Demarais et al. | |
| 2007/0167459 A1 | 7/2007 | Habashita et al. | |
| 2009/0181897 A1 | 7/2009 | Fujii et al. | |
| 2010/0143334 A1 | 6/2010 | Peled et al. | |
| 2010/0166715 A1 | 7/2010 | Peled et al. | |
| 2010/0184694 A1 | 7/2010 | Peled et al. | |
| 2010/0222256 A1 | 9/2010 | Fujii | |
| 2011/0269686 A1 | 11/2011 | Fujii et al. | |
| 2012/0094907 A1 | 4/2012 | Abraham et al. | |
| 2012/0207748 A1 | 8/2012 | Peled et al. | |

FOREIGN PATENT DOCUMENTS

| | | |
|---|---|---|
| CA | 1297007 | 3/1992 |
| EP | 0243153 | 10/1987 |
| EP | 0396158 | 11/1990 |
| EP | 0215126 | 7/1991 |
| EP | 0220520 | 9/1991 |
| EP | 0459516 | 12/1991 |

(Continued)

OTHER PUBLICATIONS

Fransen et al. Suppression of Dualtropic Human Immunodeficiency Virus Type 1 by the CXCR4 Antagonist AMD3100 is Associated with Efficiency of CXCR4 Use and Baseline Virus Composition. Antimicrob. Agents Chemother. 2008. vol. 52, Nol. 7, pp. 2608-2615.*

Hendrix et al. Safety, Pharmacokinetics, and Antiviral Activity of AMD3100, a Selective CXCR4 Receptor Inhibitor, in HIV-1 Infection. J Acquir Immune Defic Syndr. 2004, vol. 37, Nol. 2, pp. 1253-1261.*

Hesselgesser et al. Neuronal apoptosis induced by HIV-1 gp120 and the chemokine SDF-1alpha is mediated by the chemokine receptor CXCR4. Brief Communication. Current Biology. 1998, vol. 8, pp. 595-598.*

Apr. 5, 2001 Development of Specific CXCR4 Inhibitors Based on an Anti-HIV Peptide, T140, and Their Structure-Activity Relationships Study Akane Omagari et al. Peptide Science vol. 2000, No. 37th 129-132.

Sep. 14, 2000 Pharmacophore Identification of a Specific CXCR4 Inhibitor, T140, Leads to Development of Effective Anti-HIV Agents with Very High Selectivity Indexes Hirokazu Tamamura et al. Bioorganic & Medical Chemistry Letters vol. 10, No. 23 2633-2637.

(Continued)

*Primary Examiner* — Marcela M Cordero Garcia

(57) ABSTRACT

The present invention provides novel polypeptides of A1-Arg-A2-Cys-Tyr-A3-A4-X-A5-A6-Cit Cys-A7 (I) or their salts (wherein A1 is hydrogen or a residue of arginine, lysine, ornithine, citrulline, alanine, or the like; A2 is an aromatic amino acid residue; A3, A4 and A6 are each a residue of arginine, lysine, ornithine, citrulline, or alanine; A5 is a residue of tyrosine, phenylalanine, alanine, naphthylalanine, or citrulline; A7 is a lysine or arginine residue whose carboxyl group may be converted into amido; and X is a residue of D-ornithyl-proline, prolyl-D-ornithine, D-lysyl-proline, or the like, with the proviso that any one of A1, A3, A4, A5, A6 and A7 is a residue of alanine or the like or that X is citrulline or the like), and methods of using same in the treatment of HIV.

21 Claims, 2 Drawing Sheets

FOREIGN PATENT DOCUMENTS

| | | |
|---|---|---|
| EP | 0459795 | 12/1991 |
| EP | 0231819 | 4/1992 |
| EP | 0355811 | 12/1993 |
| EP | 0373679 | 6/1994 |
| EP | 0331186 | 8/1994 |
| EP | 0344796 | 9/1994 |
| EP | 0263490 | 1/1995 |
| EP | 0230980 | 3/1996 |
| EP | 0401384 | 3/1996 |
| EP | 0272703 | 10/1997 |
| EP | 0370205 | 7/1998 |
| EP | 0459630 | 8/1998 |
| EP | 0217404 | 1/1999 |
| EP | 0237545 | 8/1999 |
| EP | 0169566 | 7/2000 |
| EP | 0335423 | 3/2003 |
| EP | 1323730 | 7/2003 |
| EP | 0473268 | 10/2003 |
| EP | 2058395 | 5/2009 |
| JP | 2002-506830 | 3/2002 |
| JP | 2002-247843 | 8/2002 |
| WO | WO 91/07988 | 6/1991 |
| WO | WO 93/15211 | 8/1993 |
| WO | WO 95/10534 | 4/1995 |
| WO | WO 99/47158 | 9/1999 |
| WO | WO 00/06086 | 2/2000 |
| WO | WO 00/09152 | 2/2000 |
| WO | WO 01/38352 | 5/2001 |
| WO | WO 01/64716 | 9/2001 |
| WO | WO 01/85196 | 11/2001 |
| WO | WO 02/20561 | 3/2002 |
| WO | WO 2004/020462 | 3/2004 |
| WO | WO 2004/024178 | 3/2004 |
| WO | WO 2004/087068 | 10/2004 |
| WO | WO 2008/017025 | 2/2008 |
| WO | WO 2008/075369 | 6/2008 |
| WO | WO 2008/075370 | 6/2008 |
| WO | WO 2008/075371 | 6/2008 |
| WO | WO 2010/146578 | 12/2010 |
| WO | WO 2010/146584 | 12/2010 |
| WO | WO 2012/095849 | 7/2012 |

OTHER PUBLICATIONS

Apr. 9, 2001 Increase of R5 HIV-1 Infection and CCR5 Expression in T Cells Treated With High Concentration of CXCR4 Antagonists and SDF-1 Kazuko Gotoh et al. Journal of Infection and Chemotherapy vol. 7, No. 1 28-36.

Jun. 30, 1999 HIV-cell Fusion Inhibitors Targeted to the HIV Second Receptor: T22 and Its Downsized Analogs with High Activity Hirokazu Tamamura et al. Peptide Science vol. 1998, No. 35 49-52.

Jan. 18, 1999 A Low-Molecular-Weight Inhibitor against the Chemokine Receptor CXCR4: A Strong Anti-HIV Peptide T140 Hirokazu Tamamura et al. Biochemical and Biophysical Research Communications vol. 253, No. 3 877-882.

Oct. 16, 1997 Effective Lowly Cytotoxic Analogs of an HIV-cell Fusion Inhibitor, T22([Tyr5,12, Lys7]-polyphemusin II) Hirokazu Tamamura et al. Bioorganic & Medical Chemistry vol. 6, No. 2 231-238.

Feb. 1, 1999 T134, a Small Molecule CXCR4 Inhibitor, Has No Cross-Drug Resistance with AMD3100, a CXCR4 Antagonist with a Different Structure Rieko Arakaki et al. Journal of Virology vol. 73, No. 2 pp. 1719-1723.

Nakashima et al. "Anti-Human Immunodeficiency Virus Activity of a Novel Synthetic Peptide, T22 ([Tyr-5,12, Lys-7]Polyphemusin II): A Possible Inhibitor of Virus-Cell Fusion", Antimicrobial Agents and Chemotherapy, 36(6): 1249-1255, Jun. 1992.

Communication Pursuant to Article 96(2) EPC Dated Feb. 6, 2006 From the European Patent Office Re. Application No. 10963414.6.

Communication Pursuant to Article 96(2) EPC Dated Mar. 17, 2005 From the European Patent Office Re. Application No. 10963414.6.

Communication Pursuant to Article 96(2) EPC Dated Jul. 18, 2006 From the European Patent Office Re. Application No. 10963414.6.

Communication Pursuant to Article 96(2) EPC Dated Jul. 26, 2007 From the European Patent Office Re. Application No. 10963414.6.

Interview Summary Dated May 3, 2005 From the US Patent and Trademark Office Re. U.S. Appl. No. 10/363,209.

Interview Summary Dated Feb. 21, 2006 From the US Patent and Trademark Office Re. U.S. Appl. No. 10/363,209.

Notice of Allowance Dated Mar. 9, 2006 From the US Patent and Trademark Office Re. U.S. Appl. No. 10/363,209.

Notice of Allowance DAted May 21, 2009 From the US Patent and Trademark Office Re. U.S. Appl. No. 11/497,225.

Official Action Dated Nov. 3, 2005 From the US Patent and Trademark Office Re. U.S. Appl. No. 10/363,209.

Official Action Dated Jun. 15, 2005 From the US Patent and Trademark Office Re. U.S. Appl. No. 10/363,209.

Official Action Dated Aug. 28, 2008 From the US Patent and Trademark Office Re. U.S. Appl. No. 11/497,225.

Requisition by the Examiner Dated Mar. 8, 2011 From the Canadian Intellectual Property Office Re. Application No. 2,421,183.

Requisition by the Examiner Dated May 19, 2011 From the Canadian Intellectual Property Office Re. Application No. 2,421,183.

Requisition by the Examiner Dated Aug. 25, 2009 From the Canadian Intellectual Property Office Re. Application No. 2,421,183.

Response Dated Jul. 1, 2005 to Communication Pursuant to Article 96(2) EPC of Mar. 17, 2005 From the European Patent Office Re. Application No. 10963414.6.

Response Dated Feb. 3, 2006 to Official Action of Nov. 3, 2005 From the US Patent and Trademark Office Re. U.S. Appl. No. 10/363,209.

Response Dated Jun. 4, 2008 to Restriction Official Action of Apr. 8, 2008 From the US Patent and Trademark Office Re. U.S. Appl. No. 11/497,225.

Response Dated Sep. 7, 2011 to Requisition by the Examiner of Mar. 8, 2011 From the Canadian Intellectual Property Office Re. Application No. 2,421,183.

Response Dated May 9, 2006 to Communication Pursuant to Article 96(2) EPC of Feb. 6, 2006 From the European Patent Office Re. Application No. 10963414.6.

Response Dated Sep. 15, 2005 to Official Action of Jun. 15, 2005 From the US Patent and Trademark Office Re. U.S. Appl. No. 10/363,209.

Response Dated Nov. 16, 2007 to Communication Pursuant to Article 96(2) EPC of Jul. 26, 2007 From the European Patent Office Re. Application No. 10963414.6.

Response Dated Apr. 18, 2005 to Restriction Official Action of Mar. 18, 2005 From the US Patent and Trademark Office Re. U.S. Appl. No. 10/363,209.

Response Dated Feb. 24, 2010 to Requisition by the Examiner of Aug. 25, 2009 From the Canadian Intellectual Property Office Re. Application No. 2,421,183.

Response Dated Jan. 26, 2009 to Official Action of Aug. 28, 2008 From the US Patent and Trademark Office Re. U.S. Appl. No. 11/497,225.

Response Dated Jan. 29, 2007 to Communication Pursuant to Article 96(2) EPC of Jul. 18, 2006 From the European Patent Office Re. Application No. 10963414.6.

Response Dated Jun. 30, 2010 to Requisition by the Examiner of May 19, 2011 From the Canadian Intellectual Property Office Re. Application No. 2,421,183.

Restriction Official Action Dated Apr. 8, 2008 From the US Patent and Trademark Office Re. U.S. Appl. No. 11/497,225.

Restriction Official Action Dated Mar. 18, 2005 From the US Patent and Trademark Office Re. U.S. Appl. No. 10/363,209.

Supplementary European Search Report Dated Nov. 19, 2004 From the European Patent Office Re. Application No. 01963414.6.

Arakaki et al. "T134, A Small-Molecule CXCR4 Inhibitor, Has No Cross-Drug Resistance With AMD3100, A CXCR4 Antagonist With A Different Structure", Journal of Virology, XP002199036, 73(2): 1791-1723, Feb. 1999.

Gotoh et al. "Increase of R5 HIV-1 Infection and CCR5 Expression in T Cells Treated With High Concentrations of CXCR4 Antagonists and SDF-1", Journal of Infection and Chemotherapy, 7(1): 28-36, 2001.

Omagari et al. "Development of Specific CXCR4 Inhibitors Based on an Anti-IIIV Peptide, T140, and Their Structure-Activity Relationships Study", Peptide Science, 37: 129-132, 2000.

Tamamura et al. "A Low-Molecular-Weight Inhibitor Against the Chemokine Receptor CXCR4: A Strong Anti-HIV Peptide T140", Biochemical and Biophysical Research Communications, 253: 877-882, 1998.
Tamamura et al. "Downsizing of an HIV-Cell Fusion Inhibitor, T22 ([Tyr5,12, Lys7]-Polyphemusin II), With the Maintenance of Anti-HIV Activity and Solution Structure", Bioorganic & Medicinal Chemistry, 6: 473-479, 1998.
Tamamura et al. "Effective Lowly Cytotoxic Analogs of an HIV-Cell Fusion Inhibitor, T22 ([Tyr5,12, Lys7]-Polyplietmisin II)", Bioorganic & Medicinal Chemistry, 6: 231-238, 1998.
Tamamura et al. "HIV-Cell Fusion Inhibitors Targeted to the HIV Second Receptor: T22 and Its Downsized Analogs With High Activity", Peptide Science, 35: 49-52, 1998.
Tamamura et al. "Pharmacophore Identification of a Specific CXCR4 inhibitor, T140, Leads to Development of Effective Anti-HIV Agents With Very High Selectivity Indexes", Bioorganic & Medicinal Chemistry Letters, 10(23): 2633-2637, 2000.
Amendment Dated May 15, 2008 After Notice of Allowance of Apr. 14, 2008 From the US Patent and Trademark Office Re. U.S. Appl. No. 10/525,838.
Communication Pursuant to Article 94(3) EPC Dated Oct. 4, 2010 From the European Patent Office Re. Application No. 03791288.8.
Communication Pursuant to Article 94(3) EPC Dated Apr. 9, 2008 From the European Patent Office Re. Application No. 03791288.8.
Communication Pursuant to Article 94(3) EPC Dated Dec. 15, 2008 From the European Patent Office Re. Application No. 03791288.8.
Communication Pursuant to Article 94(3) EPC Dated Sep. 15, 2009 From the European Patent Office Re. Application No. 03791288.8.
Communication Pursuant to Rule 69 EPC—Reminder Concerning Payment of the Designation Fee (Art. 79(2) EPC) and of the Examination Fee (Art. 94(1) EPC)—and Invitation Pursuant to Rule 70a(1) EPC Dated Mar. 12, 2012 From the European Patent Office Re. Application No. 10176632.7.
Communication Under Rule 71(3) EPC Dated Apr. 16, 2012 From the European Patent Office Re. Application No. 03791288.8.
European Search Report and the European Search Opinion Dated Feb. 3, 2012 From the European Patent Office Re. Application No. 10176632.7.
International Preliminary Report on Patentability Dated Aug. 19, 2004 From the International Preliminary Examining Authority Re. Application No. PCT/JP2003/010753.
International Preliminary Report on Patentability Dated Jun. 24, 2009 From the International Bureau of WIPO Re. Application No. PCT/IL2007/001596.
International Preliminary Report on Patentability Dated Jun. 24, 2009 From the International Bureau of WIPO Re. Application No. PCT/IL2007/001598.
International Preliminary Report on Patentability Dated Dec. 29, 2011 From the International Bureau of WIPO Re. Application No. PCT/IL2010/000466.
International Search Report and the Written Opinion Dated Jun. 4, 2008 From the International Searching Authority Re. Application No. PCT/IL2007/001598.
International Search Report and the Written Opinion Dated Dec. 5, 2008 From the International Searching Authority Re. Application No. PCT/IL2007/001596.
International Search Report and the Written Opinion Dated Oct. 15, 2010 From the International Searching Authority Re. Application No. PCT/IL2010/000466.
International Search Report and the Written Opinion Dated Jun. 24, 2009 From the International Searching Authority Re. Application No. PCT/IL2007/001597.
International Search Report and the Written Opinion Dated May 30, 2012 From the International Searching Authority Re. Application No. PCT/IL2012/050008.
International Search Report Dated Nov. 4, 2003 From the International Searching Authority Re. Application No. PCT/JP2003/010753.
Notice of Allowance Dated Apr. 11, 2011 From the US Patent and Trademark Office Re. U.S. Appl. No. 12/172,007.
Notice of Allowance Dated Apr. 14, 2008 From the US Patent and Trademark Office Re. U.S. Appl. No. 10/525,838.
Office Action Dated May 4, 2010 From the Israel Patent Office Re. Application No. 199468.
Office Action Dated May 4, 2010 From the Israel Patent Office Re. Application No. 199469.
Office Action Dated Sep. 4, 2011 From the Israel Patent Office Re. Application No. 199468 and Its Translation Into English.
Office Action Dated Oct. 31, 2011 From the Israel Patent Office Re. Application No. 199469 and Its Translation Into English.
Official Action Dated Jul. 1, 2010 From the US Patent and Trademark Office Re. U.S. Appl. No. 12/172,007.
Official Action Dated May 4, 2012 From the US Patent and Trademark Office Re. U.S. Appl. No. 12/520,699.
Official Action Dated Mar. 5, 2012 From the US Patent and Trademark Office Re. U.S. Appl. No. 12/520,803.
Official Action Dated Jul. 11, 2007 From the US Patent and Trademark Office Re. U.S. Appl. No. 10/525,838.
Official Action Dated May 18, 2012 From the US Patent and Trademark Office Re. U.S. Appl. No. 13/178,737.
Official Action Dated Jan. 24, 2011 From the US Patent and Trademark Office Re. U.S. Appl. No. 12/172,007.
Official Action Dated Jun. 25, 2012 From the US Patent and Trademark Office Re. U.S. Appl. No. 12/520,811.
Requisition—Sequence Listing Dated Jan. 5, 2011 From the Canadian Intellectual Property Office Re. Application No. 2,673,719.
Requisition by the Examiner Dated Jul. 6, 2012 From the Canadian Intellectual Property Office Re. Application No. 2,421,183.
Requisition by the Examiner Dated Oct. 17, 2011 From the Canadian Intellectual Property Office Re. Application No. 2,537,158.
Requisition by the Examiner Dated May 25, 2010 From the Canadian Intellectual Property Office Re. Application No. 2,537,158.
Respone Dated Jan. 4, 2012 to Office Action of Sep. 4, 2011 From the Israel Patent Office Re. Application No. 199468 and its Translation into English.
Response Dated Nov. 1, 2010 to Official Action of Jul. 1, 2010 From the US Patent and Trademark Office Re. U.S. Appl. No. 12/172,007.
Response Dated Dec. 8, 2009 to Office Action of Aug. 11, 2009 From the Japanese Patent Office Re. Application No. 2003-301176.
Response Dated Jan. 8, 2008 to Official Action of Jul. 11, 2007 From the US Patent and Trademark Office Re. U.S. Appl. No. 10/525,838.
Response Dated Jun. 10, 2009 to Restriction Official Action of Mar. 26, 2009 From the US Patent and Trademark Office Re. U.S. Appl. No. 12/172,007.
Response Dated Oct. 12, 2010 to Communication Pursuant to Article 94(3) EPC of Oct. 4, 2010 From the European Patent Office Re. Application No. 03791288.8.
Response Dated Apr. 15, 2009 to Communication Pursuant to Article 94(3) EPC of Dec. 15, 2008 From the European Patent Office Re. Application No. 03791288.8.
Response Dated Oct. 15, 2008 to Communication Pursuant to Article 94(3) EPC of Apr. 9, 2008 From the European Patent Office Re. Application No. 03791288.8.
Response Dated Jan. 21, 2010 to Communication Pursuant to Article 94(3) EPC of Sep. 15, 2009 From the European Patent Office Re. Application No. 03791288.8.
Response Dated Oct. 21, 2010 to Office Action of May 4, 2010 From the Israel Patent Office Re. Application No. 199468.
Response Dated Oct. 21, 2010 to Office Action of May 4, 2010 From the Israel Patent Office Re. Application No. 199469.
Response Dated Mar. 22, 2011 to Requisition—Sequence Listing of Jan. 5, 2011 From the Canadian Intellectual Property Office Re. Application No. 2,673,719.
Response Dated Mar. 23, 2011 to Official Action of Jan. 24, 2011 From the US Patent and Trademark Office Re. U.S. Appl. No. 12/172,007.
Response Dated May 25, 2007 to Restriction Official Action of Feb. 6, 2007 From the US Patent and Trademark Office Re. U.S. Appl. No. 10/525,838.
Response Dated Nov. 25, 2011 to Requisition by the Examiner of May 25, 2010 From the Canadian Intellectual Property Office Re. Application No. 2,537,158.
Response Dated Jan. 31, 2011 to Office Action of Oct. 19, 2010 From the Japanese Patent Office Re. Application No. 2003-301176.

Restriction Official Action Dated Mar. 1, 2012 From the US Patent and Trademark Office Re. U.S. Appl. No. 12/520,699.
Restriction Official Action Dated Feb. 6, 2007 From the US Patent and Trademark Office Re. U.S. Appl. No. 10/525,838.
Restriction Official Action Dated Feb. 16, 2012 From the US Patent and Trademark Office Re. U.S. Appl. No. 13/178,737.
Restriction Official Action Dated Mar. 26, 2009 From the US Patent and Trademark Office Re. U.S. Appl. No. 12/172,007.
Restriction Official Action Dated Dec. 28, 2011 From the US Patent and Trademark Office Re. U.S. Appl. No. 12/520,803.
Restriction Official Action Dated Mar. 28, 2012 From the US Patent and Trademark Office Re. U.S. Appl. No. 12/520,811.
Second Amendment Dated Jul. 14, 2008 to Amendment of May 15, 2008 After Notice of Allowance of Apr. 14, 2008 From the US Patent and Trademark Office Re. U.S. Appl. No. 10/525,838.
Supplementary Partial European Search Report Dated Nov. 28, 2007 From the European Patent Office Re. Application No. 03791288.8.
Translation of Office Action Dated Aug. 11, 2009 From the Japanese Patent Office Re. Application No. 2003-301176.
Translation of Office Action Dated Oct. 19, 2010 From the Japanese Patent Office Re. Application No. 2003-301176.
AACR "97th Annual Meeting 2006: Publications", AACR, American Association of Cancer Research, Retreived From the Internet, 2006.
Auerbach et al. "Angiogenesis Assays: Problems, Pitfalls and Potential", Cancer and Metastasis Reviews, 19: 167-172, 2000.
Avniel et al. "Involvement of the CXCL12/CXCR4 Pathway in the Recovery of Skin Following Burns", Journal of Investigative Dermatology, 126(2): 468-476, 2006.
Balkwill "The Significance of Cancer Cell Expression of the Chemokine Receptor CXCR4", Seminars in Cancer Biology, 14: 171-179, 2004.
Bork "Powers and Pitfalls in Sequence Analysis: The 70% Hurdle", Genome Research, 10: 398-400, 2000.
Brenner "Errors in Genome Annotation", Trends in Genetics, TIG, 15(4): 132-133, Apr. 1999.
Broxmeyer et al. "Rapid Mobilization of Murine and Human Hematopoietic Stem and Progenitor Cells With AMD3100, A CXCR4 Antagonist", The Journal of Experimental Medicine, 201(8): 1307-1318, Apr. 18, 2005.
Burger et al. "Small Peptide Inhibitors of the CXCR4 Chemokine Receptor (CD184) Antagonize the Activation, Migration, and Antiapoptotic Responses of CXCL12 in Chronic Lymphocytic Leukemia B Cells", Blood, 106(5): 1824-1830, Sep. 1, 2005.
Dar et al. "Chemokine Receptor CXCR4-Dependent Internalization and Resecretion of Functional Chemokine SDF-1 by Bone Marrow Endothelial and Stromal Cells", Nature Immunology, 6(10): 1038-1046, Oct. 2005.
Darash-Yahana et al. "Role of High Expression Levels of CXCR4 in Tumor Growth, Vascularization, and Metastatis", The FASEB Journal, 18: 1240-1242, 2004. p. 1242, Last Para.
Di Cesare et al. "In Vitro Characterization and Inhibition of the CXCR4/CXCL12 Chemokine Axis in Human Uveal Melanoma Cell Lines", Cancer Cell International, XP021036445, 7(17): 1-8, Nov. 14, 2007. Abstract, Last Para, Title, p. 5, Right Col., Last Para.
Doerks et al. "Protein Annotation: Detective Work for Function Predicition", Trends in Genetics, 14(6): 248-250, Jun. 1998.
Esler et al. "Renal Sympathetic Denervation in Patients With Treatment-Resistant Hypertension (The Symplicity HTN-2 Trial): A Randomised Controlled Trial", The Lancet, 376: 1903-1909, Published Online Nov. 17, 2010.
Flomenberg et al. "The Use of AMD3100 Plus G-CSF for Autologous Hematopoietic Progenitor Cell Mobilization Is Superior to G-CSF Alone", Blood, 106(5): 1867-1874, 2005.
Fujii et al. "Peptide-Lead CXCR4 Antagonists With High Anti-HIV Activity", Current Opinion in Investigational Drugs, 2(9): 1198-1202, 2001.
Ghobrial et al. "Molecular Mechanisms Involved in Homing and Migration of Plasma Cells in Response to CXCR4", Blood, XP002629051, 104(11): 1-33, Apr. 12, 2005.
Gura "Cancer Models: Systems for Identifying New Drugs Are Often Faulty", Science, 278(5340): 1041-1042, Nov. 7, 1997.

Hatse et al. "CXC-ChemokineReceptor 4 as A Potential New Therapeutic Target for Neuroblastoma and Breast Cancer", International Journal of Cancer, XP001156644, Supplement, 13: 349, Abstract # p. 669, Jul. 2002.
Heredia et al. "Rapamycin Causes Down-Regulation of CCR5 and Accumulation of Anti-HIV Beta-Chemokines: An Approach to Suppress R5 Strains of HIV-1", Proc. Natl. Acad. Sci. USA, PNAS, 100(18): 10411-10416, Sep. 2, 2003.
Hiramatsu et al. "Synthesis of CXCR4 Antagonists, T140 Derivatives With Improved Biostability, and Their SAR Study", Peptide Science, XP009092185, 203: 213-216, 2002. Abstract, Fig.1.
Jain "Barriers to Drug Delivery in Solid Tumors. Many Tumors Resist Full Penetration by Anticancer Agents. Such Resistance May Help Explain Why Drugs That Eradicate Tumor Cells in Laboratory Dishes Often Fail to Eliminate Malignancies in the Body", Scientific American, p. 58-65, Jul. 1994.
Kim et al. "In Vitro Behavior of Hematopoietic Progenitor Cells Under the Influence of Chemoattractants: Stromal Cell-DErived Factor-1, Steel Factor, and the Bone Marrow Environment", Blood, 91(1): 100-110, 1998.
Kollet et al. "Human CD34+CXCR4—Sorted Cells Harbor Intracellular CXCR4, Which Can Be Functionally Expressed and Provide NOD/SCID Repopulation", Blood, 100(8): 2778-2786, 2002.
Koshiba et al. "Expression of Stromal Cell-Derived Factor 1 and CXCR4 Ligand Receptor System in Pancreatic Cancer: A Possible Role for Tumor Progression", Clinical Cancer Research, 6(9): 3530-3535, Sep. 2000.
Lack et al. "A Pharmacokinetic-Pharmacodynamic Model for the Mobilization of CD34+ Hematopoietic Progenitor Cells by AMD3100", Clinical Pharmacology and Therapeutics, 77(5): 427-436, 2005.
Lapidot et al. "How Do Stem Cells Find Their Way Home?", Blood, 106(6): 1901-1910, 2005.
Lapidot et al. "The Essential Roles of the Chemokine SDF-1 and Its Receptor CXCR4 in Human Stem Cell Homing and Repopulation of Transplanted Immune-Deficient NOD/SCID and NOD/SCID/B2m<Null> Mice", Leukemia, 16(10): 1992-2003, 2002.
Levesque et al. "Disruption of the CXCR4/CXCL12 Chemotactic Interaction During Hematopoietic Stem Cell Mobilization Induced by GCSF or Cyclophosphamide", Journal of Clinical Investigation, 111(2): 187-196, Jan. 2003.
Martin et al. "Chemokines Acting Via CXCR2 and CXCR4 Control the Release of Neutrophils From the Bone Marrow and Their Return Following Senescence", Immunity, 19(4): 583-593, Oct. 2003.
Matthys et al. "AMD3100, A Potent and Specific Antagonist of the Stromal Cell-Derived Factor-1 Chemokine Receptor CXCR4, Inhibits Autoimmune Joint Inflammation in IFN-Gamma Receptor-Deficient Mice", The Journal of Immunology, 167(8): 4686-4692, 2001.
Menu et al. "The Involvement of Stromal Derived Factor 1Alpha in Homing and Progression of Multiple Myeloma in the 5TMM Model", Haematologica/The Hematology Journal, 91(5): 605-612, 2006.
Merck "Clinical Aspects of Cancer", The Merck Manual, Jun. 26, 2007.
Merck "Introduction: Overview of Cancer", The Merck Manual, Jun. 26, 2007.
Merck "Rheumatoid Arthritis (RA)", The Merck Manual, 18th Ed., 2005.
Mori et al. "Involvement of Stromal Cell-Derived Factor 1 and CXCR4 Receptor System in Pancreatic Cancer", Gastroenterology, XP009021758, 122(4/Suppl.1): A490, Abstract #T1608, Apr. 2002.
Mueller et al. "Involvement of Chemokine Receptors in Breast Cancer Metastasis", Nature, 410: 50-56, Mar. 2001.
Nagasawa et al. "Molecular Cloning and Structure of a Pre-B-Cell Growth-Stimulating Factor", Proc. Natl. Acad. sci. USA, 91: 2305-2309, Mar. 1994.
Neidl "Failure Modes in the Discovery Process", Cancer Drug Design and Discovery, Chap.18.2.2: 427-431, 2008.
Ngo et al. "Computational Complexity, Protein Structure Prediction, and the Levinthal Paradox", The Protein Folding Problem and Tertiary Structure Prediction, Chap.14: 433-440, 492-495, 1994.

Peled et al. "Dependence of Human Stem Cell Engraftment and Repopulation of NOD/SCID Mice on CXCR4", Science, 283(5403): 845-848, 1999.

Phillips et al. "Epidermal Growth Factor and Hypoxia-Induced Expression of CXC Chemokine Receptor 4 on Non-Small Cell Lung Cancer Cells Is Regulated by the Phosphatidylinositol 3-Kinase/PTEN/AKT/Mammalian Target of Rapamycin Signaling Pathway and Activation of Hypoxia Inducible Factor-1Alpha", The Journal of Biological Chemistry, 280(23): 22473-22481, 2005.

Phillips et al. "The Stromal Derived Factor-1/CXCL12-CXC Chemokine Receptor 4 Biological Axis in Non-Small Cell Lung Cancer Metastasis", 167: 1676-1686, 2003.

Princen et al. "HIV Chemokine Receptor Inhibitors as Novel Anti-HIV Drugs", Cytokine & Growth Factor Reviews, 16(6): 659-677, 2005.

Ratajczak et al. "T140 Enhances G-CSF-Induced Mobilization of Hematopoietic Stem Cells", Experimental Hematology, 31: 154, Abstract #280, 2003.

Rossi et al. "The Biology of Chemokines and Their Receptors", Annual Reviews of Immunology, 18: 217-242, 2000.

Skolnick et al. "From Genes to Protein Structure and Function: Novel Applications of Computational Approaches in the Genomic Era", Trends in Biotechnology, TIBTECH, 18(1): 34-39, Jan. 2000.

Sporn et al. "Chemoprevention of Cancer", Carcinogenesis, 21(3): 525-530, 2000.

Tamamura "Development of Selective Antagonists Against an HIV Second Receptor", Yakugaku Zasshi, 121(11): 781-792, 2001. Abstract in English.

Tamamura et al. "A Future Perspective on the Development of Chemokine Receptor CXCR4 Antagonists", Database EMBASE [Online], XP002675634, Database Accession No. EMB-2008509452, Oct. 2008. & Expert Opinion on Drug Discovery, 3(10): 1155-1166, Oct. 2008.

Tamamura et al. "A Low-Molecular-Weight Inhibitor Against the Chemokine Receptor CXCR4: A Strong Anti-HIV Paptide T140", Biochemical and Biophysical Research Communications, 253(3): 877-882, 1998.

Tamamura et al. "A Low-Molecular-Weight Inhibitor Against the Chemokine Receptor CXCR4: A Strong Anti-HIV Peptide T140", Biochemic and Biophysical Research Communications, XP002169961, 253(3): 877-882, Jan. 1, 1998. Abstract, Fig.1.

Tamamura et al. "Certification of the Critical Importance of L-3-(2-Naphtyl)Alanine at Position 3 of a Specific CXCR4 Inhibitor, T140, Leads to an Exploratory Performance of Its Downsizing Study", Bioorganic & Medicinal Chemistry, 10: 1417-1426, 2002.

Tamamura et al. "Development of Specific CXCR4 Inhibitors Possessing High Selectivity Indexes as Well as Complete Stability in Serum Based on an Anti-HIV Peptide T140", Bioorganic & Medicinal Chemistry Letters, XP002265743, 11(14): 1897-1902, Jul. 23, 2001. Abstract, Fig.1, p. 1901, r-h col., Last Sentence Before 'Acknowledgements'.

Tamamura et al. "Downsizing of an HIV-Cell Fusion Inhibitor, T22 ([Tyr5,12, Lys7]-Polyphemusin II), With the Maintenance of Anti-HIV Activity and Solution Structure", Bioorganic & Medicinal Chemistry, XP002458598, 6(4): 473-479, Apr. 1998. Abstract, Fig.1.

Tamamura et al. "Effective Lowly Cytotoxic Analogs of an HIV-Cell Fusion Inhibitor, T22 ([Tyr5,12, Lys7]-Polyphemusin II)", Bioorganic & Medicinal Chemistry, XP002906341, 6(2): 231-238, Jan. 1, 1998. Abstract, Fig.1.

Tamamura et al. "Efficient Analogs of an Anti-HIV Peptide, T22 ([Tyr5,12, Lys7]-Polyphemusin II), Having Low Cytotoxicity", Peptide Science—Present and Future, Proceedings of the 1st International Peptide Symposium, XP002973954, 1997: 427-429, Jan. 1, 1999. Abstract, Fig.2.

Tamamura et al. "Enhancement of the T140-Based Pharmacophores Leads to the Development of More Potent and Bio-Stable CXCR4 Antagonists", Organic Biomolecular Chemistry, 1: 3663-3669, 2003.

Tamamura et al. "T140 Analogs as CXCR4 Antagonists Identified as Anti-Metastatic Agents in the Treatment of Breast Cancer", FEBS Letters, 550: 79-83, 2003.

Tamamura ct al. "T140 Analogs as CXCR4 Antagonists Identified as Anti-Metastatic Agents in the Treatment of Breast Cancer", FEBS Letters, XP004448372, 550: 79-83, Aug. 28, 2003.

Tamamura et al. "The Therapeutic Potential of CXCR4 Antagonists in the Treatment of HIV Infection, Cancer Metastasis and Rheumatoid Arthritis", Expert Opinion of Therapeutic Targets, 9(6): 1267-1282, 2005.

Tsutsumi et al. "Therapeutic Potential of the Chemokine Receptor CXCR4 Antagonists as Multifunctional Agents", Biopolymers (Peptide Science), XP002629052, 88(2): 279-289, 2006.

Ulvatne et al. "Short Antibacterial Peptides and Erythromycin Act Synergically Against *Escherichia coli*", Journal of Antimicrobial Chemotherapy, 48: 203-208, 2001.

Weekes et al. "Stromal Derived Factor1Alpha Mediates Resistance to mTOR Inhibition by the Preservation of Hypoxia Inducible Factor-1Alpha (HIF-1Alpha) Expression", Proceedings of the Annual Meeting of the American Association for Cancer Research, AACR, 47: 553, Abstract #2341, 2006.

Wells "Additivity of Mutational Effects in Proteins", Biochemistry, 29(37): 8509-8517, Sep. 18, 1990.

Zannettino et al. "Elevated Scrum Levels of Stromal-Derived Factor-1Alpha Arc Associated With Increased Osteoclast Activity and Osteolytic Bone Disease in Multiple Myeloma Patients", Cancer Research, 65(5): 1700-1709, Mar. 1, 2005. Abstract, p. 1707, Last Para-p. 1708, First Para.

Zhou et al. "CXCR4 Is a Major Chemokine Receptor on Glioma Cells and Mediates Their Survival", The Journal of Biological Chemistry, 277(51): 49481-49487, Dec. 29, 2002.

Zuluaga et al. "Neutropenia Induced in Outbred Mice by a Simplified Low-Dose Cyclophosphamide Regimen: Characterization and Applicability to Diverse Experimental Models of Infectious Diseases", BMC infectious Diseases, 6(55): 1-10, Mar. 17, 2006.

Official Action Dated Dec. 7, 2012 From the US Patent and Trademark Office Re. U.S. Appl. No. 12/520,699.

Official Action Dated Sep. 5, 2012 From the US Patent and Trademark Office Re. U.S. Appl. No. 12/520,699.

Official Action Dated Sep. 12, 2012 From the US Patent and Trademark Office Re. U.S. Appl. No. 12/520,803.

Kucia et al. "Trafficking of Normal Stem Cells and Metastasis of Cancer Stem Cells Involve Similar Mechanisms: Pivotal Role of the SDF-1—CXCR4 Axis", Stem Cells, 23(7): 879-894, Aug. 2005.

Voermans et al. "Migratory Behavior of Leukemic Cells From Acute Myeloid Leukemia Patients", Leukemia, 16(4): 650-657, Apr. 2002.

Advisory Action Before the Filing of an Appeal Brief Dated Nov. 16, 2012 From the US Patent and Trademark Office Re. U.S. Appl. No. 12/520,699.

Notice of Allowance Dated Dec. 10, 2012 From the US Patent and Trademark Office Re. U.S. Appl. No. 13/178,737.

* cited by examiner

POLYPEPTIDE ANTI-HIV AGENT CONTAINING THE SAME

FIELD OF THE INVENTION

The present invention relates to a novel polypeptide and to methods of using same as an anti-HIV virus agent.

BACKGROUND OF THE INVENTION

Since antiviral activity of an endotoxin-affinity polypeptide separated from horseshoe crab (*Tachypleus* genus, *Limulus* genus and *Carcinoscopius* genus) has been found out (Japanese Provisional Patent Publication No. 2-167230 and Japanese PCT Provisional Patent Publication No. 2-500194), many attempts to synthesize novel antiviral polypeptides have been carried out by chemical modification thereof, reducing a molecular weight thereof and modifying a part of the structure of the above-mentioned polypeptide (WO92/04374, Japanese Provisional Patent Publication No. 5-163298 and Japanese PCT Provisional Patent Publication No. 8-504837). In recent years, it has been found out that novel low molecular weight antiviral polypeptides T134 and T140 are polypeptides having low cytotoxicity and having excellent anti-HIV virus activity (H. Tamamura et. al.; Biochemical and Biophysical Research Commun., 253, 877-882 (1998)). However, these T134 and T140 were not practical for a medical use.

Accordingly, an object of the present invention is to provide a polypeptide having excellent anti-HIV virus activity and low cytotoxicity.

The present inventor has earnestly carried out studies to solve the above-mentioned problems. As a result, he has found out that a novel polypeptide shows an excellent anti-HIV virus activity and has low cytotoxicity, in which a part of amino acids of T140, which has conventionally been known to inhibit infection of HIV by specifically binding to a CXCR4 ligand, is substituted with other amino acids, whereby he has accomplished the present invention.

SUMMARY OF THE INVENTION

That is, the present invention relates to a novel polypeptide represented by the following formula (I):

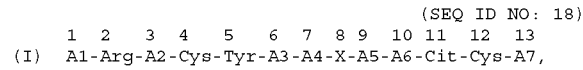

(SEQ ID NO: 18)

(wherein

A1 represents a hydrogen atom, or an arginine, lysine, ornithine, citrulline or alanine residue or a residue of N-α-substituted derivative of these amino acids;

A2 represents an aromatic amino acid residue;

A3, A4 and A6 each independently represent an arginine, lysine, ornithine, citrulline or alanine residue;

A5 represents a tyrosine, phenylalanine, alanine, naphthylalanine or citrulline residue;

A7 represents a lysine or arginine residue in which a carboxyl group may be amidated;

X represents a peptide residue represented by the following formula (a):

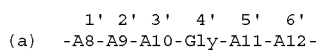

SEQ ID NO: 29

(wherein

A8 and A12 each independently represent an alanine, valine, leucine, isoleucine, serine, cysteine or methionine residue;

A9 represents an aromatic amino acid residue, A10 is selected from the same amino acid residues as in A3, A11 represents a tyrosine, phenylalanine, tryptophane, alanine, valine, leucine, isoleucine, serine, cysteine or methionine residue, provided that when both of the 1'-position and the 6'-position are cysteine residues, they may be bonded by a disulfide bond), or a peptide residue selected from the group consisting of a D-ornithyl-proline, prolyl-D-ornithine, D-lysyl-proline, prolyl-D-lysine, D-arginyl-proline, prolyl-D-arginine, D-citrullyl-proline, D-citrullyl-alanine, D-alanyl-citrulline, prolyl-D-citrulline, glycyl-ornithine, ornithyl-glycine, glycyl-lysine, lysyl-glycine, glycyl-arginine, arginyl-glycine, glycyl-citrulline, citrullyl-glycine, D-alanyl-proline, and D-lysyl-alanine, and a hydrogen atom of a side chain ω-amino group of D-arginine, L-arginine, D-lysine, L-lysine, D-ornithine or L-ornithine which are constitutional amino acids of said peptide residues may be substituted by a ω-aminoacyl group, and these peptide residues represent a peptide residue which binds amino acid residues at the 7-position and the 9-position through a peptide bond;

wherein Arg represents an arginine residue, Cys represents a cysteine residue, Tyr represents a tyrosine residue, Cit represents a citrulline residue, Gly represents a glycine residue, and the cysteine residues at the 4-position and the 12-position may be bonded by a disulfide bond;

provided that, in the above polypeptide or a salt thereof, either of the amino acid residues of A1, A3, A4, A5 and A6 is an alanine or citrulline residue; or X represents a peptide residue containing a D-citrulline, D-alanine, citrulline or alanine residue)

or a salt thereof.

In the polypeptides of the formula (I) of the present invention, A1 is preferably an arginine, alanine or citrulline residue; A2 is preferably a tryptophane or naphthylalanine residue; A3 is preferably arginine, alanine or citrulline residue; A4 is preferably a lysine, alanine or citrulline residue; X is preferably a D-lysyl-proline, D-alanyl-proline, D-lysyl-alanine or D-citrullyl-proline residue; A5 is preferably a tyrosine or alanine residue; A6 is preferably an arginine, alanine or citrulline residue; A7 is preferably an arginine residue.

Specific examples of the most preferred polypeptide of the present invention is a polypeptide of the formula (I) wherein A1, A6 and A7 are arginine residues, A2 is a naphthylalanine residue, A3 is a citrulline residue, A4 is a lysine residue, X is a D-lysyl-proline residue, and A5 is a tyrosine residue (SEQ ID NO: 11), a polypeptide of the formula (I) wherein A1, A3, A6 and A7 are arginine residues, A2 is a naphthylalanine residue, A4 is a lysine residue, X is a D-citrullyl-proline residue, and A5 is a tyrosine residue (SEQ ID NO:13), a polypeptide of the formula (I) wherein A1, A6 and A7 are arginine residues, A2 is a naphthylalanine residue, A3 is a citrulline residue, A4 is a lysine residue, X is a D-citrullyl-proline residue, A5 is a tyrosine residue (SEQ ID NO: 15), and a polypeptide of the formula (I) wherein A1 is a citrulline residue, A2 is a naphthylalanine residue, A3, A6 and A7 are arginine residues, A4 is a lysine residue, X is a D-citrullyl-proline residue, A5 is a tyrosine residue (SEQ ID NO: 16).

As another embodiment of the preferred polypeptide according to the present invention, there may be exemplified by a polypeptide of the formula (I) wherein A1, A6 and A7 are arginine residues, A2 is a naphthylalanine residue, A3 is a alanine residue, A4 is a lysine residue, X is a D-lysyl-proline residue, and A5 is a tyrosine residue (SEQ ID NO: 4), a polypeptide of the formula (I) wherein A1 is a citrulline residue, A2 is a naphthylalanine residue, A3, A6 and A7 are arginine residues, A4 is a lysine residue, X is a D-lysyl-proline residue, and A5 is a tyrosine residue (SEQ ID NO: 10), a polypeptide of the formula (I) wherein A1, A3 and A7 are arginine residues, A2 is a naphthylalanine residue, A4 is a lysine residue, X is a D-lysyl-proline residue, A5 is a tyrosine residue, and A6 is a citrulline residue (SEQ ID NO: 14), a polypeptide of the formula (I) wherein A1 and A3 are citrulline residues, A2 is a naphthylalanine residue, A4 is a lysine residue, X is a D-lysyl-proline residue, A5 is a tyrosine residue, A6 and A7 are arginine residues (SEQ ID NO: 19), and a polypeptide of the formula (I) wherein A1, A3 and A7 are arginine residues, A2 is a naphthylalanine residue, A4 is a lysine residue, X is a D-citrullyl-proline residue, A5 is a tyrosine residue, and A6 is a citrulline residue (SEQ ID NO: 17).

Incidentally, in the polypeptide of the present invention, the amino acid of A7 is preferably one in which the carboxyl group is amidated in view of improving stability of the polypeptide in vivo such as in serum, etc.

According to certain particular embodiments, the polypeptide has an amino acid sequence as set forth in formula (I), wherein one of the amino acid residues of A1, A3, A4, A5, A6 and A7 is an alanine or citrulline residue; or X is a peptide residue including a D-citrulline, D-alanine, citrulline, or alanine residue or a salt thereof. According to other particular embodiments, the polypeptide has an amino acid sequence as set forth in formula (I), wherein one of the amino acid residues of A1, A3, A4, A5, A6 and A7 is an alanine or citrulline residue. In other embodiments, the polypeptide has an amino acid sequence as set forth in formula (I), wherein X is a peptide residue including a D-citrulline, D-alanine, citrulline, or alanine residue (e.g. wherein X is D-alanyl-proline, D-lysyl-alanine or D-citrullyl-proline). According to certain additional particular embodiments, the polypeptide has an amino acid sequence as set forth in formula (I), wherein one of the amino acid residues of A1, A3, A4, A5, A6 and A7 is an alanine or citrulline residue; and X is a peptide residue including a D-citrulline, D-alanine, citrulline, or alanine residue.

According to other particular embodiments, the polypeptide has an amino acid sequence as set forth in formula (I), wherein one of the amino acid residues of A1, A3, A4, A5, A6 and A7 is an alanine residue. In other embodiments, the polypeptide has an amino acid sequence as set forth in formula (I), wherein X is a peptide residue including a D-alanine or alanine residue. According to other particular embodiments, the polypeptide has an amino acid sequence as set forth in formula (I), wherein one of the amino acid residues of A1, A3, A4, A5, A6 and A7 is a citrulline residue. In other embodiments, the polypeptide has an amino acid sequence as set forth in formula (I), wherein X is a peptide residue including a D-citrulline or citrulline residue.

Specific examples of the polypeptides of the present invention are shown in the following Table 1 together with the conventionally known polypeptides T134 and T140.

TABLE 1

| SEQ ID NO. | | 1 (A1) ① | 2 ② | 3 (A2) ③ | 4 ④ | 5 ⑤ | 6 (A3) ⑥ | 7 (A4) ⑦ | 8 X ⑧ | 9 (A5) ⑨ | 10 (A6) ⑩ | 11 ⑪ | 12 (A7) ⑫ | 13 ⑬ |
|---|---|---|---|---|---|---|---|---|---|---|---|---|---|---|
| 1 | T134* | H-Arg- | Arg- | Trp- | Cys- | Tyr- | Arg- | Lys- | DLys- | Pro- | Tyr- | Arg- | Cit- | Cys-Arg-OH |
| 2 | T140* | H-Arg- | Arg- | Nal- | Cys- | Tyr- | Arg- | Lys- | DLys- | Pro- | Tyr- | Arg- | Cit- | Cys-Arg-OH |
| 3 | TA14001 | H-Arg- | Arg- | Nal- | Cys- | Tyr- | Arg- | Lys- | DLys- | Pro- | Tyr- | Arg- | Cit- | Cys-Arg-OH |
| 4 | TA14005 | H-Arg- | Arg- | Nal- | Cys- | Tyr- | Ala- | Lys- | DLys- | Pro- | Tyr- | Arg- | Cit- | Cys-Arg-OH |
| 5 | TA14006 | H-Arg- | Arg- | Nal- | Cys- | Tyr- | Arg- | Ala- | DLys- | Pro- | Tyr- | Arg- | Cit- | Cys-Arg-OH |
| 6 | TA14007 | H-Arg- | Arg- | Nal- | Cys- | Tyr- | Arg- | Lys- | DAla- | Pro- | Tyr- | Arg- | Cit- | Cys-Arg-OH |
| 7 | TA14008 | H-Arg- | Arg- | Nal- | Cys- | Tyr- | Arg- | Lys- | DLys- | Ala- | Tyr- | Arg- | Cit- | Cys-Arg-OH |
| 8 | TA14009 | H-Arg- | Arg- | Nal- | Cys- | Tyr- | Arg- | Lys- | DLys- | Pro- | Ala- | Arg- | Cit- | Cys-Arg-OH |
| 9 | TA14010 | H-Arg- | Arg- | Nal- | Cys- | Tyr- | Arg- | Lys- | DLys- | Pro- | Tyr- | Ala- | Cit- | Cys-Arg-OH |
| 10 | TC14001 | H-Cit- | Arg- | Nal- | Cys- | Tyr- | Arg- | Lys- | DLys- | Pro- | Tyr- | Arg- | Cit- | Cys-Arg-OH |
| 20 | TC14003 | H-Arg- | Arg- | Nal- | Cys- | Tyr- | Cit- | Lys- | DLys- | Pro- | Tyr- | Arg- | Cit- | Cys-Arg-OH |
| 11 | TN14003 | H-Arg- | Arg- | Nal- | Cys- | Tyr- | Cit- | Lys- | DLys- | Pro- | Tyr- | Arg- | Cit- | Cys-Arg-NH$_2$ |
| 12 | TC14004 | H-Arg- | Arg- | Nal- | Cys- | Tyr- | Arg- | Cit- | DLys- | Pro- | Tyr- | Arg- | Cit- | Cys-Arg-OH |
| 21 | TC14005 | H-Arg- | Arg- | Nal- | Cys- | Tyr- | Arg- | Lys- | DLys- | Pro- | Tyr- | Arg- | Cit- | Cys-Arg-OH |
| 13 | TN14005 | H-Arg- | Arg- | Nal- | Cys- | Tyr- | Arg- | Lys- | DCit- | Pro- | Tyr- | Arg- | Cit- | Cys-Arg-NH$_2$ |
| 14 | TC14006 | H-Arg- | Arg- | Nal- | Cys- | Tyr- | Arg- | Lys- | DLys- | Pro- | Tyr- | Cit- | Cit- | Cys-Arg-OH |
| 15 | TC14011 | H-Arg- | Arg- | Nal- | Cys- | Tyr- | Cit- | Lys- | DCit- | Pro- | Tyr- | Arg- | Cit- | Cys-Arg-OH |
| 22 | TC14012 | H-Arg- | Arg- | Nal- | Cys- | Tyr- | Arg- | Lys- | DCit- | Pro- | Tyr- | Arg- | Cit- | Cys-Arg-NH$_2$ |
| 16 | TC14018 | H-Cit- | Arg- | Nal- | Cys- | Tyr- | Arg- | Lys- | DCit- | Pro- | Tyr- | Arg- | Cit- | Cys-Arg-NH$_2$ |

*公知polypeptide

In the polypeptide of the above-mentioned formula, respective symbols mean amino acid residues shown by three-letter code internationally admitted, and all amino acids mean L-amino acids otherwise it is shown as D-amino acid in which the character "D" is put in front of said three-letter code, Nal represents L-3-(2-naphthyl)alanine, and Cit represents L-citrulline [=2-amino-5-ureidovalerianic acid].

In another aspect, the present invention demonstrates that the novel polypeptides of the invention are particularly useful as anti-HIV agents, as they provide increased selectivity (i.e. increased antiviral activity and/or reduced cytotoxicity) compared to known antiviral agents such as T140 and T134 as well as to AZT, a commercially available antiviral drug which was clinically approved for HIV therapy.

In one embodiment, there is provided a method for inhibiting HIV infection in a subject in need thereof, comprising contacting cells of the subject with an effective amount of a polypeptide of the invention, thereby inhibiting HIV infection in said subject.

In another embodiment, the invention provides a method for treating a subject in need of an anti-HIV therapy, comprising contacting cells of the subject with an effective amount of a polypeptide of the invention, thereby treating said subject.

In another embodiment, there is provided a method for preventing or reducing HIV-induced cell death, comprising contacting cells of a subject in need thereof with an effective amount of a polypeptide of the invention, thereby preventing or reducing HIV-induced death of the cells.

In various embodiments, the polypeptide has an amino acid sequence as set forth in formula (I), as defined herein. According to currently preferable embodiments, the polypeptide has an amino acid sequence as set forth in any one of SEQ ID NOs: 3-16 and 20-22. According to certain particular embodiments, the sequence of the polypeptide is as set forth in any one of SEQ ID NOs: 11, 13, 15, 20 and 22. In other particular embodiments, the sequence of the polypeptide is as set forth in any one of SEQ ID NOs: 3-10, 12, 14, 16 and 21. It should be understood, that the use of T140 and T134, which are known in the art to manifest anti-HIV properties, is explicitly excluded from the scope of the present invention.

In another embodiment, the cells are peripheral blood mononuclear cells. In another embodiment, the cells are CD4$^+$ T cells. In another embodiment, the cells are CXCR4 expressing cells. In another embodiment, the cells are contacted with the polypeptide ex vivo. In another embodiment, the cells are contacted with the polypeptide in vivo. In another embodiment, the polypeptide is administered to said subject in the form of a pharmaceutical composition further comprising a physiologically acceptable carrier. In another embodiment, the polypeptide is conjugated to a reverse transcriptase inhibitor, an HIV protease inhibitor or an in-vivo half-time elongating substance.

Other objects, features and advantages of the present invention will become clear from the following description and drawings.

DETAILED DESCRIPTION OF THE INVENTION

Figure 1:
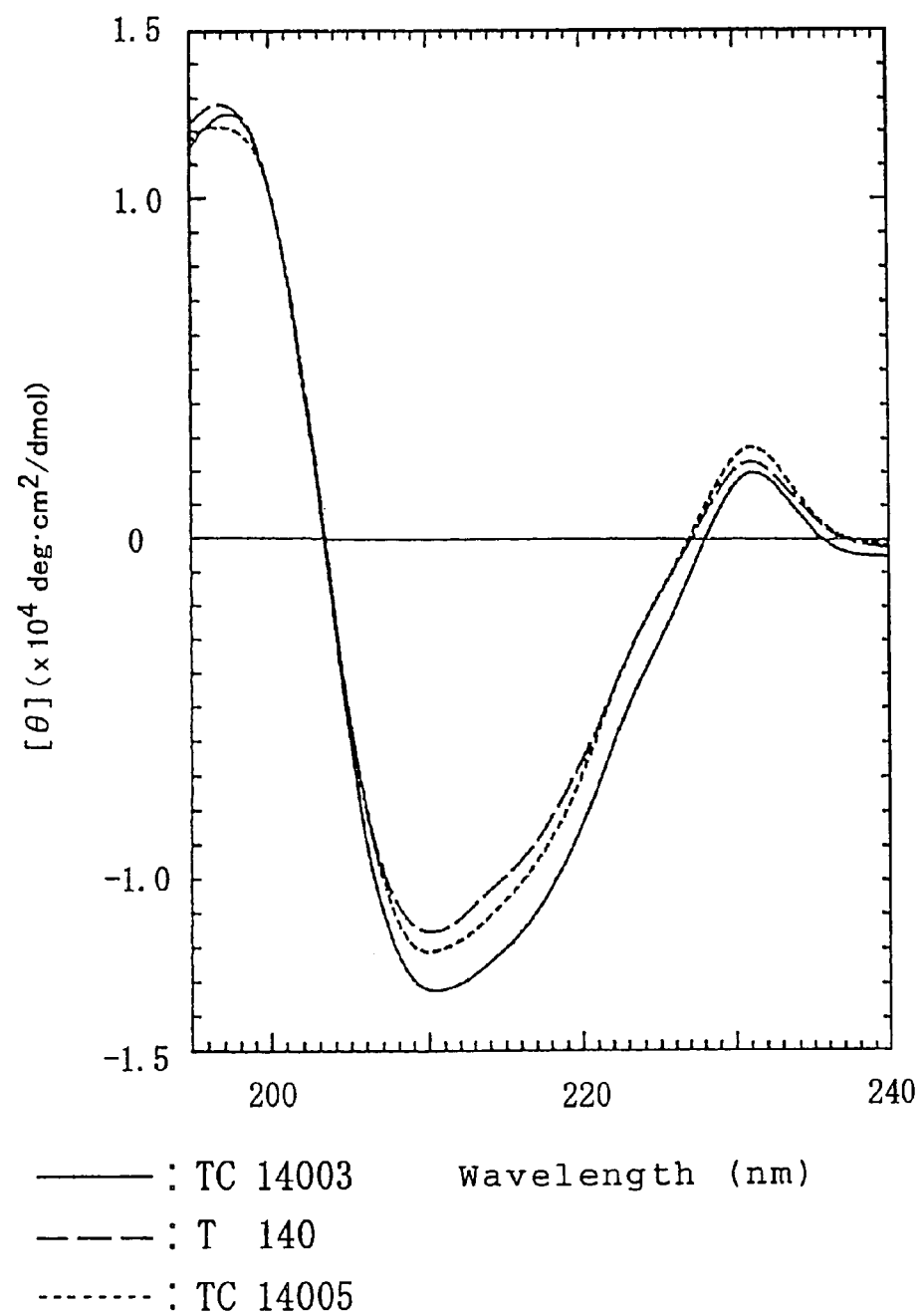
FIG. 1 is CD spectra of polypeptides TC14003 and TC14005 of the present invention, and T140.

The polypeptide of the formula (I) according to the present invention can be produced by a polypeptide synthetic method, for example, a solid phase peptide synthesis, a liquid phase peptide synthesis and the like. In the solid phase synthesis, the peptide can be produced by, for example, bonding a carboxyl group of a N-protected arginine (or lysine) in which an α-amino group of an amino acid corresponding to A7 is protected by an urethane type protecting group such as 9-fluorenylmethyloxycarbonyl (Fmoc) group, etc., to an insoluble resin through a spacer which is optionally capable of bonding to the carboxyl group (that is, the carboxyl group of arginine (or lysine) is converted into p-carboxymethylbenzyl ester), then, removing the protecting group for the α-amino group, linking N-protected cysteine thereto, and carrying out condensation of amino groups successively to an amino terminus direction in the same manner as mentioned above. In other words, the protected amino acids corresponding to the 12-position to the 1-position of the amino acid sequence shown by the following formula (I) are successively linked according to the solid phase synthesis, then, the protecting groups bound to the insoluble resin and respective amino acids are eliminated to obtain the straight chain polypeptide of the present invention represented by the above-mentioned formula (I). Moreover, in the obtained polypeptide, two cysteines at the 4-position and the 12-position can form a disulfide bond (—S—S—) through a mercapto group.

```
                                                    (SEQ ID NO: 18)
      1   2   3    4   5   6  7  8  9  10  11  12   13
(I)  A1-Arg-A2-Cys-Tyr-A3-A4-X-A5-A6-Cit-Cys-A7,
```

(wherein

A1 represents a hydrogen atom or an arginine, lysine, ornithine, citrulline or alanine residue, or a residue of N-α-substituted derivative of these amino acids;

A2 represents an aromatic amino acid residue, preferably a tyrosine, phenylalanine, tryptophane or naphthylalanine residue;

A3, A4 and A6 each independently represent an arginine, lysine, ornithine, citrulline or alanine residue;

A5 represents a tyrosine, phenylalanine, alanine, naphthylalanine or citrulline residue;

A7 represents a lysine or arginine residue in which the carboxyl group may be amidated;

X represents a peptide residue represented by the following formula (a):

```
        1'  2'  3'   4'  5'  6'         SEQ ID NO: 29
(a)   -A8-A9-A10-Gly-A11-A12-
```

(wherein

A8 or A12 represents an alanine, valine, leucine, isoleucine, serine, cysteine or methionine residue;

A9 represents an aromatic amino acid residue, A10 is selected from the same amino acid residues as in A3, A11 represents a tyrosine, phenylalanine, tryptophane, alanine, valine, leucine, isoleucine, serine, cysteine or methionine residue, provided that when both of the 1'-position and the 6'-position are cysteine residues, these may be bonded by a disulfide bond), or a peptide residue selected from the group consisting of D-ornithyl-proline, prolyl-D-ornithine, D-lysyl-proline, prolyl-D-lysine, D-arginyl-proline, prolyl-D-arginine, D-citrullyl-proline, prolyl-D-citrulline, D-citrullyl-alanine, D-alanyl-citrulline, glycyl-ornithine, ornithyl-glycine, glycyl-lysine, lysyl-glycine, glycyl-arginine, arginyl-glycine, glycyl-citrul-line, citrullyl-glycine, D-alanyl-proline, and D-lysyl-alanine, and a hydrogen atom of a side chain w-amino group of D-arginine, L-arginine, D-lysine, L-lysine, D-ornithine or L-ornithine which are constitutional amino acids of said peptide residues may be substituted by a ω-acylamino group, and these peptide residues represent a peptide residue which binds amino acid residues at the 7-position and the 9-position through a peptide bond;

wherein, Arg represents an arginine residue, Cys represents a cysteine residue, Tyr represents a tyrosine residue, Cit represents a citrulline residue, Gly represents a glycine residue;

in the above-mentioned polypeptide or a salt thereof, either of the amino acid residues of A1, A3, A4, A5 and A6 is an alanine or citrulline residue, or;

X is a peptide residue containing a D-citrulline, D-alanine, citrulline or alanine residue).

As the above-mentioned insoluble resin having an amino group, any material may be used so long as it is capable of binding to a carboxyl group of an N-protected arginine (or lysine) at the C-terminus or a spacer (a cross-linking group) optionally bonding thereto, and capable of being eliminated after synthesis of a polypeptide.

As such an insoluble resin, there may be mentioned, for example, Alko resin (p-benzyloxyalcohol resin), a benzhydrylamine resin, a methylbenzhydrylamine resin, an aminomethylphenoxymethyl resin, a Fmoc-NH-SAL resin [(4-(2',4'-dimethoxyphenyl-Fmoc-aminoethyl)phenoxy linker resin), H. Rink, Tetrahedron Lett., 28: 3787 (1987), 0.68 mmole/g] and derivatives of these materials, etc. When these resins are used, an objective material can be directly obtained therefrom by cleavage in either of the cases, and in view of a yield, Alko resin or a Fmoc-NH-SAL resin is preferred.

As the above-mentioned spacer optionally bonding to the carboxyl group of the amino acid at the C-terminus, there may be mentioned a spacer having a functional group capable of bonding to the carboxyl group and a carboxyl group, and there may be mentioned, for example, that which can convert the carboxyl group of arginine (or lysine) to a p-carboxymethylbenzyl ester, but it is not specifically limited.

The protected amino acid to be used for synthesis of the polypeptide of the present invention means an amino acid whose functional group is protected by a protecting group according to the conventionally known method, and various kinds of protected amino acid are commercially available. When the polypeptide of the present invention is to be synthesized, either of the protecting groups shown below is preferably selected. First, as the protecting group for an α-amino group of an amino acid, Boc (t-butyloxycarbonyl) or Fmoc (9-fluorenylmethyloxycarbonyl) is preferred. As the protecting group for a guanidino group of arginine (Arg), Tos (tosyl), $NO_2$ (nitro), Mtr (4-methoxy-2,3,6-trimethylbenzenesulfonyl), Pmc (2,2,5,7,8-pentamethylchroman-6-sulfonyl) or Pbf (2,2,4,6,7-penta-hydroxydihydrobenzofuran-6-sulfonyl) is preferred. As the protecting group for a mercapto group of cysteine, there may be mentioned Bzl (benzyl), 4-MeOBzl (4-methoxybenzyl), 4-MeBzl (4-methylbenzyl), Acm (acetamidomethyl), Trt (trityl), Npys (3-nitro-2-pyridinesulfenyl), t-Bu (t-butyl) and t-Bus (t-butylthio), and 4-MeBzl, Acm, or Npys is preferred. As the protecting group for a hydroxyl group of tyrosine (Tyr), Bzl, $Cl_2$Bzl (2,6-dichlorobenzyl) or t-Bu may be mentioned, or it may not be protected. As the protecting group for an ε-amino group of lysine (Lys), there may be mentioned Z (benzyloxycarbonyl), 2-ClZ (2-chlorobenzyloxycarbonyl), Boc or Npys. It is preferred that the respective protecting groups are selected from the already known protecting groups, depending on the synthetic conditions of a peptide.

In synthesis of a peptide, linking of a protected amino acid can be carried out according to an ordinary condensation method such as DCC (dicyclohexylcarbodiimide) method, DIPCDI (diisopropylcarbodiimide) method [Tartar, A. et. al.: J. Org. Chem. 44, 5000 (1979)], active ester method, mixed or symmetric acid anhydride method, carbonyl-diimidazole method, DCC-HOBt (1-hydroxybenzotriazole) method [Keonig, W. et. al.: Chem. Ber., 103, 788, 2024, 2034 (1970)], diphenylphosphorylazide method and the like, and the DCC method, DCC-HOBt method, DIPCDI-HOBt method or symmetric acid anhydride method is preferred. These condensation reactions are generally carried out in an organic solvent such as dichloromethane, dimethylformamide, etc., or in a mixed solvent of the above-mentioned solvents. As the eliminating reagent of the protecting group for an α-amino group, there may be used trifluoroacetic acid/dichloromethane, HCl/dioxane, piperidine/dimethylformamide, etc., and they are suitably selected depending on the kind of said protecting group. Also, a degree of the progress of the condensation reaction at respective stages of synthesis can be examined by a method of E. Kaiser, et. al. [Anal, Biochem., 34, 595 (1970)] (ninhydrin reaction method).

As described above, a protected polypeptide having a desired amino acid sequence can be obtained.

When an aminomethyl resin derivative is used as the insoluble resin, the protected polypeptide can be eliminated from said resin by, for example, treating with ammonia in a suitable solvent. Subsequently, by treating the resulting material by hydrogen fluoride, polypeptide amide in which all the protecting groups are eliminated shown by the above formula can be obtained. When a benzhydrylamine resin, methylbenzhydrylamine resin, aminomethylphenoxymethyl resin or DMBHA resin [Funakoshi. S. et. al.; J. Chem. Soc., Chem. Commun., 1988, 382] is used as the insoluble resin, said resin and the protecting groups are simultaneously eliminated by treating it with hydrogen fluoride, TFMSA (trifluoromethane sulfonic acid) [published by Academic Press, edited by E. Gross, Yajima, H.; "The Peptides" vol 5, P65 (1983)], TMSOTf (trimethylsilyltrifurate) [Fujii, N. et. al.; J. Chem. Soc., Che. Commun., 1987, 274] or TMSBr (trimethylsilyl bromide) [Fujii, N. et. al.; Chem. Pharm. Bull., 35, 3880 (1987)] and the like.

Further, a cyclic polypeptide can be obtained by reducing with 2-mercaptoethanol, DTT (dithiothreitol), etc. to make a mercapto group of cysteine a reduced type, if desired, and then, subjecting to oxidation treatment to form a disulfide bond.

For the oxidation treatment, a method already known in the art can be used, and oxygen in air or an oxidizing agent such as ferricyanate (for example, potassium ferricyanide) is usually employed.

Incidentally, an anti-HIV substance is bonded to the above-mentioned polypeptide which is in a state of bonding to a resin, to form a complex of the polypeptide according to the present invention and the anti-HIV substance. As the above-mentioned anti-HIV substance, there may be mentioned, for example, a reverse transcriptase inhibitor, a HIV protease inhibitor and the like.

As the above-mentioned reverse transcriptase inhibitor, there may be mentioned a substance which inhibits activity of reverse transcriptase of HIV, and nucleoside type and non-nucleoside type substances may be mentioned. As the nucleoside type inhibitor, a nucleoside or an analogue thereof constituted by either of a base selected from a pyrimidine base, a purine base, an imidazole base and a triazole base, and a furanose having at least one hydroxyl group or its acyclo derivative is preferred, and there may be mentioned, for example, AZT (CAS REGISTRY NUMBERS: 30516-87-1: zidovudine), ddI (CAS REGISTRY NUMBERS: 69655-05-6: didanosine), ddC (CAS REGISTRY NUMBERS: 7481-89-2: zalcitabine), 2',3'-didehydro-2',3'-dideoxythymidine (CAS REGISTRY NUMBERS: 3056-17-5: d4T: stavudine), 3'-thia-2',3'-dideoxycytidine (CAS REGISTRY NUMBERS: 134678-17-4: 3TC: lamivudine), 2'-β-fluoro-ddC, 3'-fluorothymidine (CAS REGISTRY NUMBERS: 25526-93-6: FLT), 9-(2-phosphonyl-methoxyethyl)-adenine (CAS REGISTRY NUMBERS: 106941-25-7: PMEA), 6-Cl-ddI, 6-Cl-ddC, and the like.

Also, as the non-nucleoside type inhibitors, there may be mentioned, for example, tetrahydro-imidazo-benzo-diazepin-one or -thione (TIBO) derivative (more specifically, (+)-S-4,5,6,7-tetrahydro-5-methyl-6-(3-methyl-2-butenyl)imidazo[4,5,1-jk][1,4]benzodiazepin-2(1H)-thione) (CAS REGISTRY NUMBERS: 167206-29-3: R82913), hydroxyethoxy-methylphenylthiothymine (HEPT) derivative, Nevirapine (CAS REGISTRY NUMBERS: 129618-40-2), pyridinone derivative, and the like.

In consideration of easiness of binding to the above-mentioned polypeptide and an effective inhibition mechanism of DNA synthesis by being taken into DNA, a nucleoside type reverse transcriptase inhibitor is preferred among these, and among the nucleoside type HIV reverse transcriptase inhibitors, preferred are AZT, ddI, ddC, d4T or 3TC which have already been administered to human clinically, and more preferred is AZT in which antiviral activity thereof is particularly and synergistically strengthened when it is chemically bonded to said polypeptide to form a substance of the present invention. These nucleoside type reverse transcriptase inhibitors, etc. are taken into DNA when HIV synthesizes DNA from RNA by reverse transcription, and as a result, it inhibits synthesis of DNA, therefore, a unnatural type nucleoside or nucleoside analogue is preferred. The above-mentioned nucleoside analogue means a non-nucleoside compound having a similar stereostructure to that of the nucleoside. Also, as these reverse transcriptase inhibitors, those commercially available or prepared according to the known synthetic method can be used.

Further, as the HIV protease inhibitor, it is a substance which inhibits an activity of protease of HIV, and preferably an inhibitor which is a substrate transition-state mimic compound of said protease. The substrate transition-state mimic compound means a substance capable of binding to a substrate binding domain of an enzyme and a substance having a similar stereostructure as that of a substrate in an enzyme-substrate complex. There may be mentioned, for example, Ro 31-8959 (CAS REGISTRY NUMBERS: 127779-20-8: saquinavir), A-77003 (CAS REGISTRY NUMBERS: 134878-17-4), A-80987 (CAS REGISTRY NUMBERS: 144141-97-9), KNI-93 (CAS REGISTRY NUMBERS: 138258-64-7), KNI-102 (CAS REGISTRY NUMBERS: 139694-65-8), KNI-174, KNI-227 (CAS REGISTRY NUMBERS: 147384-69-8), KNI-272 (CAS REGISTRY NUMBERS: 147318-81-8), L-735527 (CAS REGISTRY NUMBERS: 150378-17-9: indinavir), SC-52151 (CAS REGISTRY NUMBERS: 143224-34-4: Telinavir), VX-478, ABT-538 (CAS REGISTRY NUMBERS: 155213-67-5: ritonavir), DMP-323 (CAS REGISTRY NUMBERS: 151867-81-1), U-96988 (CAS REGISTRY NUMBERS: 149394-65-0), and the like. More preferably, Ro 31-8959, L-735527 and KN-272 having high antiviral activity are preferred but it is not specifically limited. As these HIV protease inhibitors, those commercially available or prepared according to the known synthetic method can be used. With regard to Ro 31-8959, there may be mentioned, for example, a preparation method described in J. Med. Chem. 36, p. 2300-2310 (1993).

In the above-mentioned complex, the above-mentioned polypeptide and the above-mentioned anti-HIV activity substance are chemically bonded, and the bond is not specifically limited so long as the bond is chemically formed. Specifically, there may be mentioned an ester bond, amide bond, ether bond, disulfide bond, etc. Of these, the ester bond is a bond capable of being cleaved by an intracellular esterase, etc. after the bonded anti-HIV activity substance is transferred to a target cell in vivo, so that said anti-HIV activity substance is released at a proximity of an action site of the anti-HIV activity substance, and the bond having a stability to an extent which is not easily cleaved in the course of transfer to the target cell. Accordingly, the ester bond is most preferred.

As a preparation method of the above-mentioned complex, for example, it is possible to prepare a complex of the polypeptide and the anti-HIV substance such as AZT, etc., by forming a bond between the amino terminus or the carboxy terminus of the polypeptide and the above-mentioned anti-HIV substance in an organic solvent such as pyridine, etc. For preparing such a complex, a spacer such as succinic acid or glutaric acid, etc. can be used between the polypeptide and the anti-HIV substance. In such a case, for example, an acid anhydride of succinic acid or glutaric acid is used and these carboxylic acids form an ester bond with the anti-HIV substance such as AZT, etc. in the presence of dimethylaminopyridine, and then, the resulting complex and an α-amino group or ω-amino group of the N-terminal amino acid of the polypeptide which is bound to the above-mentioned resin can be linked. It is also possible to prepare a material, in advance, in which a dendrite spacer (for example, polylysine, etc.) is linked to an arginine residue at the amino terminus of the polypeptide according to the present invention, and then, to condense the material by a conventionally known method (for example, DIPCI-HOBt method) to link them.

Incidentally, according to the same method as the linking process of the above-mentioned anti-HIV substance, it is also possible to elongate a half-life of the substance according to the present invention in vivo by linking, to the substance of the present invention, an in vivo half-life elongation substance such as polyethylene glycol (U.S. Pat. No. 5,342,940, etc.) or its derivative, glycosaminoglycan (U.S. Pat. No. 5,310,881, U.S. Pat. No. 4,585,754, etc.) such as chondroitin, etc., lipids such as lecithin (U.S. Pat. No. 5,109,118, No. 5,310,958, No. 5,362,491, etc.), etc., or styrene derivative polymer (Polym. J., 17:567, 1985, etc.) to which various kinds of oligosaccharides are bound, etc.

The polypeptide thus obtained can be isolated and purified by an isolation and purification means of a polypeptide which are conventionally known per se., such as extraction, recrystallization, various kinds of chromatographies (gel filtration, ion-exchange, distribution, adsorption, reverse phase), electrophoresis, counter current distribution, etc., particularly a method by reverse phase high performance liquid chromatography is most effective.

Also, the thus obtained polypeptide is considered to have endotoxin binding ability, antibacterial activity, endotoxin-sensitized hematocyte hemolysis and antiviral activity as in the conventionally known polypeptide derived from horseshoe crab, T134 and T140, and it was shown to have particularly good antiviral activity to human immunodeficiency virus (HIV), and its cytotoxicity is markedly reduced as compared to the conventional T134 and T140.

The polypeptide represented by the formula (I) according to the present invention shows basic property due to the characteristic feature of the amino acids constituting it, therefore, it may be in the form of a salt formed by acid addition. For example, the polypeptide represented by the formula (I) forms a salt with an inorganic acid (hydrochloric acid, hydrobromic acid, phosphoric acid, nitric acid, sulfuric acid, etc.), an organic carboxylic acid (acetic acid, propionic acid, maleic acid, succinic acid, malic acid, citric acid, tartaric acid, salicylic acid, etc.) or an organic sulfonic acid (methanesulfonic acid, p-toluenesulfonic acid, etc.). The polypeptide represented by the formula (I) according to the present invention can be used as an effective ingredient of a medical composition as a pharmaceutically acceptable salt.

Incidentally, the polypeptide of the formula (I) has a function of specifically binding to a CXCR4 ligand, and according to this specificity, it can be considered to have an anti-HIV virus activity. It can be also considered, in addition to anti-HIV virus agent, to utilize the same as a medical composition for treatment of cancer, acute lymphoma, osterosarcoma, heterotopia osteogenesis, rheumatism, etc., which are diseases in which a CXCR4 ligand is involved.

In certain embodiments, the present invention provides therapeutic and prophylactic methods of using the novel polypeptides of the invention e.g. as anti-HIV agents. Thus, the polypeptides of the invention may be used in methods for treating or preventing HIV infection.

In one embodiment, there is provided a method for inhibiting HIV infection in a subject in need thereof, comprising contacting cells of the subject with an effective amount of a polypeptide having an amino acid sequence as set forth in any one of SEQ ID NOs: 3-16 and 20-22.

In another embodiment, the invention provides a method for treating a subject in need of an anti-HIV therapy, comprising contacting cells of the subject with an effective amount of a polypeptide having an amino acid sequence as set forth in any one of SEQ ID NOs: 3-16 and 20-22.

In another embodiment, there is provided a method for preventing or reducing HIV-induced cell death, comprising contacting cells of a subject in need thereof with an effective amount of a polypeptide having an amino acid sequence as set forth in any one of SEQ ID NOs: 3-16 and 20-22.

In various embodiments, the polypeptide has an amino acid sequence as set forth in any one of SEQ ID NOs: 3-16 and 20-22. According to certain particular embodiments, the sequence of the polypeptide is represented by any one of SEQ ID NOs: 11, 13, 15, 20 and 22. In other particular embodiments, the sequence of the polypeptide is represented by any one of SEQ ID NOs: 3-10, 12, 14, 16 and 21. Included within the scope of the present invention are polypeptides represented by any one of SEQ ID NOs: 3-16 and 20-22, as well as variants thereof retaining substantially the same activity (e.g. about 0.5 to 20 times, or in other embodiments about 0.5 to 2 times of the anti-HIV activity) and substantially the same amino acid sequence (e.g. 1-3 conservative amino acid substitutions, i.e. replacements which do not significantly alter the structure or biological activity of the peptide, such as substitutions of basic amino acids with other basic amino acids etc) as defined in Formula (I) herein.

In another embodiment, the cells are peripheral blood mononuclear cells. In another embodiment, the cells are CD4$^+$ T cells. In another embodiment, the cells are CXCR4 expressing cells. In another embodiment, the cells are contacted with the polypeptide ex vivo. In another embodiment, the cells are contacted with the polypeptide in vivo. Thus, in certain embodiments, the methods of the invention include administering to the subject an effective amount of a pharmaceutical composition comprising the polypeptide. In another embodiment, the polypeptide is conjugated to a reverse transcriptase inhibitor, an HIV protease inhibitor or an in-vivo half-time elongating substance.

The active compounds described above may be formulated for administration in a pharmaceutical carrier in accordance with known techniques. See, e.g., Remington, The Science and Practice of Pharmacy (9$^{th}$ Ed. 1995). In the manufacture of a pharmaceutical formulation according to the invention, the active compound (including the physiologically acceptable salts thereof) is typically admixed with, inter alia, a physiologically acceptable carrier. The carrier must, of course, be acceptable in the sense of being compatible with any other ingredients in the formulation and must not be deleterious to the patient. The carrier may be a solid or a liquid, or both. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 1 or 10 mg to about 100 milligrams, 1 gram or 10 grams of the compound (e.g. polypeptide) or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, Pharmaceutical Research 3 (6):318 (1986)) and typically take the form of an optionally buffered aqueous solution of the active compound. Suitable formulations comprise citrate or bis-tris buffer (pH 6) or ethanol/water and contain from 0.1 to 0.2M active ingredient.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. As indicated, the pharmaceutical compositions of the present invention may be lyophilized using techniques well known in the art.

Pharmaceutical compositions suitable for use in the context of the present invention include compositions wherein the active ingredients are contained in an amount effective to achieve the intended purpose. In some embodiments, an "effective amount" means an amount of active ingredients (e.g., a polypeptide of the invention) effective to prevent, alleviate, or ameliorate symptoms of a disorder (e.g., HIV infection) or prolong the survival of the subject being treated.

Determination of an effective amount is well within the capability of those skilled in the art, especially in light of the detailed disclosure provided herein.

For any preparation used in the methods of the invention, the dosage or the therapeutically effective amount can be estimated initially from in vitro and cell culture assays (e.g. as described in the Examples herein). For example, a dose can be formulated in animal models to achieve a desired concentration or titer. Such information can be used to more accurately determine useful doses in humans.

The data obtained from in vitro toxicity and activity and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Dosage amount and administration intervals may be adjusted individually to provide sufficient plasma levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved.

For example, suitable doses for ex-vivo methods may be determined from Table 3 herein. Suitable doses for in vivo administration my range, for example, from about 0.01 to 300 mg/kg, when administered topically, subcutaneously, orally or by intravenous injection. The amount of a composition to be administered will be dependent on the subject being treated, the severity of the affliction, the manner of administration, the judgment of the prescribing physician, etc.

In various embodiments of the present invention, the subject is selected from humans and non-human mammals. In a preferable embodiment, the subject is human.

The following examples are presented in order to more fully illustrate some embodiments of the invention. They should, in no way be construed, however, as limiting the broad scope of the invention.

EXAMPLES

Preparation of Polypeptide

Preparation of Polypeptide TC14005 (SEQ ID NO: 13)
H-Arg-Arg-NaI-Cys-Tyr-Arg-Lys-DCit-Pro-Tyr-Arg-Cit-Cys-Arg-OH (TC14005)

1. Synthesis of Protected Polypeptide TC14005 Resin

After a Fmoc group was removed by 20% piperidine/DMF, from 270 mg (0.2 mmol) of Fmoc-Arg(Pbf)-OH (0.74 mg/g) of Alko resin to which arginine had been introduced at the 14-position (which is the 13-position of the formula (I)) Fmoc-Cys (Trt)-OH (2.5 eq) which corresponds to the 13-position (which is the 12-position of the formula (I)) was added to the Alko resin, and a condensation reaction was carried out by the DIPCDI-HOBt method in DMF. A degree of progress of the condensation reaction was examined by a ninhydrin test of Kaiser. E et al. (Anal. Biochem., 34:595 (1970)).

2. Introduction of Amino Acids at 12-Position to 1-Position

In the same manner as mentioned above, Cit, Arg(Pbf), Tyr(t-Bu), Pro, D-Cit, Lys(Boc), Arg(Pbf), Tyr(t-Bu), Cys (Trt), NaI, Arg(Pbf) and Arg(Pbf) residues were successively introduced to the DMBHA resin to obtain a functional group-protected polypeptide (I) resin.

3. Deprotection of the Protecting Groups, Separation and Purification of the Polypeptide from Resin A Fmoc group was removed from the functional group-protected polypeptide (1) resin by 20% piperidine/DMF treatment, and then, the resin was reacted in 1M-TMSBr-thioanisol/TFA (trifluoroacetic acid) system (10 ml of trifluoroacetic acid containing m-cresol (100 eq) and ethanedithiol (300 eq)) per 100 mg of the resin at 25° C. for 2 hours. The resin was collected by filtration from the reaction mixture, and washed twice with 1 ml of trifluoroacetic acid, 100 ml of ice-cooled dry ether was added to the combined solution of the filtrate and the washed solution, formed precipitates were separated by centrifugation, and the residue was separated from a supernatant by decantation. The obtained residue was washed with cooled ether, and dissolved in 10 ml of 4N acetic acid, 830 mg (80 eq) of dithiothreitol was added to the solution, and the resulting mixed solution was stirred overnight. The reaction mixture was centrifuged, the supernatant was treated by Sephadex G-10 (available from Pharmacia Co.: 3.7×50 cm), and subjected to gel filtration with 4N acetic acid, and a main eluted portion which was a passed through fraction were collected, and lyophilized to obtain powder state partially purified uncyclized polypeptide TC14005.

4. Cyclization by Air Oxidation

A half amount of the above-mentioned polypeptide was adjusted to pH 7.5 with conc. aqueous ammonia, and air oxidation was carried out by passing air through the mixture to carry out cyclization. After completion of the air oxidation, the cyclized polypeptide was adsorbed to 10 g of DIAION HP-20 resin (available from Mitsubishi Chemical Co., Ltd.), and then, subjected to desorption and elution by using 60% acetonitrile (in 1N acetic acid). Said eluent was concentrated under reduced pressure at room temperature to remove acetonitrile, and further lyophilized to make powder. Further, said powder was dissolved in water, and purified by HPLC (Cosmodule 5C18ARII column: acetonitrile gradient elution) to obtain a polypeptide with a single peak. Purity thereof was confirmed by HPLC.

$[\alpha]D$ (c. 0.1: $H_2O$): +42.73

Ion spray mass spectrum (IS-MS): ($C_{90}H_{140}N_{34}O_{19}S_2$) Calculated value: 2066.43, Measured value: 2067

(triple-stage quadrupole mass spectrum analyzer APIII (Perkin-Elmer Scie X)

Preparation of Polypeptide TC14012 (SEQ ID NO: 15)

H-Arg-Arg-NaI-Cys-Tyr-Cit-Lys-DCit-Pro-Tyr-Arg-Cit-Cys-Arg-NH$_2$ (TC14012)

1. Synthesis of Protected Polypeptide TC14012 Resin

After a Fmoc group of 1.47 g (1 mmole) of Fmoc-NH-SAL resin (0.68 mmole/g) was removed by 20% piperidine/DMF, Fmoc-Arg(Pbf)-OH (2.5 eq) which corresponds to the 14-position was added to the NH-SAL resin and the resulting mixture was subjected to condensation reaction by DIPCDI-HOBt.

2. Introduction of Amino Acids at 13-Position to 1-Position

In the same manner as mentioned above, Cys(Trt), Cit, Arg(Pbf), Tyr(t-Bu), Pro, D-Cit, Lys(Boc), Cit, Tyr(t-Bu), Cys(Trt), NaI, Arg(Pbf), Arg(Pbf) residues were successively introduced to the NH-SAL resin to obtain a functional group-protected polypeptide resin.

Thereafter, in the same manner as in the synthesis of TC14005, deprotection of the protecting group, separation and purification of the polypeptide from the resin were carried out and cyclization was carried out by air oxidation to obtain TC14012.

Yielded amount: 1.432 g (Yield: 59%)

$[\alpha]D$ (c 0.41: $H_2O$): −60.67

Ion spray mass spectrum (IS-MS): ($C_{90}H_{140}N_{34}O_{19}S_2$) Calculated value: 2066.43, Measured value: 2065.73

(triple-stage quadrupole mass spectrum analyzer APIII (Perkin-Elmer Scie X)

In the same manner as mentioned above, other polypeptides of the present invention shown in Table 1 were synthesized and their IS-MS results are shown in the following Table 2.

|  | Formula | IS-MS (Calculated value) | IS-MS (Measured value) |
| --- | --- | --- | --- |
| TA14001 | $C_{87}H_{134}N_{30}O_{18}S_2$ | 1952.33 | 1952 |
| TA14005 | $C_{87}H_{134}N_{30}O_{18}S_2$ | 1952.33 | 1953 |
| TA14006 | $C_{87}H_{134}N_{32}O_{18}S_2$ | 1980.34 | 1981 |
| TA14007 | $C_{87}H_{134}N_{32}O_{18}S_2$ | 1980.34 | 1981 |
| TA14008 | $C_{87}H_{139}N_{33}O_{18}S_2$ | 2011.40 | 2012 |
| TA14009 | $C_{84}H_{137}N_{33}O_{17}S_2$ | 1945.34 | 1948 |
| TA14010 | $C_{87}H_{134}N_{30}O_{18}S_2$ | 1952.33 | 1953 |
| TC14001 | $C_{90}H_{140}N_{32}O_{19}S_2$ | 2038.42 | 2039 |
| TC14003 | $C_{90}H_{140}N_{32}O_{19}S_2$ | 2038.42 | 2038 |
| TC14004 | $C_{90}H_{140}N_{34}O_{19}S_2$ | 2066.43 | 2067 |
| TC14006 | $C_{90}H_{140}N_{32}O_{19}S_2$ | 2038.42 | 2037 |
| TC14011 | $C_{90}H_{139}N_{33}O_{20}S_2$ | 2067.42 | 2068 |
| TC14018 | $C_{90}H_{140}N_{34}O_{19}S_2$ | 2066.43 | 2066 |
| TC14020 | $C_{90}H_{140}N_{34}O_{19}S_2$ | 2066.43 | 2066 |
| TN14003 | $C_{90}H_{141}N_{33}O_{18}S_2$ | 2037.43 | 2038 |
| TN14005 | $C_{90}H_{141}N_{35}O_{18}S_2$ | 2065.45 | 2066 |

Incidentally, as an optical rotation, the following values were obtained.

TC14003: $[\alpha]D$ (c. 0.1: $H_2O$): 0
TC14011: $[\alpha]D$ (c. 0.1: $H_2O$): −47.61
TC14018: $[\alpha]D$ (c. 0.1: $H_2O$): −25.51
TC14020: $[\alpha]D$ (c. 0.1: $H_2O$): −41.74
TN14003: $[\alpha]D$ (c. 0.1: $H_2O$): −37.09
TN14005: $[\alpha]D$ (c. 0.1: $H_2O$): −27.58

CD spectra of the polypeptide TC14003 and TC14005 according to the present invention were measured. By using J-720 spectropolarimeter (manufactured by JASCO Co.) and using 1 cm cell, samples were measured with a distance of 1 nm five times, and an average value of the 5 times was obtained, and the results are shown in FIG. 1 with the CD spectra of the conventional T140. Minus peak at around 210 nm and plus peak at around 197 nm were observed, so that it was clarified that these peptides have β-sheet structure.

<Anti-HIV Activity and Cytotoxicity>

HIV-1 (IIIB) strain obtained from MOLT/HIV-1 (IIIB) cell previously infected by HIV-1 was used. The polypeptide of the present invention was added to MT-4 CD4$^+$ T cells infected by HIV in various kinds of concentrations, and a number of living cells after culturing at 37° C. for 5 days was determined by using a 3'-(4,5-dimethylthiazol-2-yl)-2,5-diphenyltetrazolinium bromide (MTT) method. Anti-HIV activity is shown by a concentration ($EC_{50}$ value), where MT-4 cell death by HIV infection is inhibited by 50%. Cytotoxicity of the peptide according to the present invention was shown by a 50% survival concentration (Test I: $CC_{50}$ value) by culturing virus-uninfected MT-4 cells with the polypeptide according to the present invention in various concentrations, and determining a number of living cells by the MTT method. Moreover, a number of living cells of human peripheral blood mononuclear cells (monocyte) (PBMC) was determined by trypan blue dyeing method, and shown by a 50% survival concentration (Test II: $CC_{50}$ value). Respective ratios of the $CC_{50}$ value and the $EC_{50}$ value were shown as a selective index (SI). Obtained values were summarized in Table 3 using the conventionally known polypeptides T134 and T140, and an anti-HIV compound: 3'-azido-2',3'-dideoxythymidine (AZT) used as a medicine as a control anti-HIV agent.

| | | | | | SI | |
| --- | --- | --- | --- | --- | --- | --- |
| | | $EC_{50}$ | $CC_{50}$ (μM) | | $CC_{50}$ (Test I)/ | $CC_{50}$ (Test II)/ |
| Compound | Charge | (nM) | (Test I) | (Test II) | $EC_{50}$ | $EC_{50}$ |
| T134 | 7 | 8.3 | >>1 | 190 | >>120 | 23000 |
| T140 | 7 | 3.3 | >>1 | 96 | >>300 | 29000 |
| TA14001 | 6 | 56 | >40 | N.T. | >750 | N.T. |
| TA14005 | 6 | 9.3 | >40 | N.T. | >4500 | N.T. |
| TA14006 | 6 | 47 | >80 | N.T. | >1800 | N.T. |
| TA14007 | 6 | 16 | >80 | N.T. | >5200 | N.T. |
| TA14008 | 7 | 17 | >80 | N.T. | >4700 | N.T. |
| TA14009 | 7 | 17 | >80 | N.T. | >4500 | N.T. |
| TA14010 | 6 | 18 | >80 | N.T. | >4800 | N.T. |
| TC14003 | 6 | 2.8 | >80 | 310 | >29000 | 160000 |
| TC14004 | 6 | 16 | >80 | 270 | >5000 | 16000 |
| TC14005 | 6 | 4.0 | >80 | 280 | >20000 | 69000 |
| TC14006 | 6 | 15 | >80 | 310 | >5300 | 20000 |
| TC14011 | 5 | 0.5 | >100 | N.T. | >200000 | N.T. |
| TC14012 | 6 | 0.4 | >100 | N.T. | >250000 | N.T. |
| TC14018 | 6 | 1.2 | >100 | N.T. | >83000 | N.T. |
| TC14020 | 6 | 2.7 | >100 | N.T. | >37000 | N.T. |
| TN14003 | 6 | 0.6 | >100 | N.T. | >166000 | N.T. |
| TN14005 | 6 | 4.6 | >100 | N.T. | >21000 | N.T. |
| AZT | | 48 | 190 | <20 | 4000 | <410 |

Charge is a number of total positive charges of the respective peptides; all the values are an average of measured values taken at least three times; and NT shows that no test was carried out.

From the above-mentioned table, it is clear that the compounds of the present invention, particularly TC14003, TC14005, TC14020 and TN14005 have substantially the same anti-HIV activity as that of the conventionally known T140, and cytotoxicity is markedly lowered. Moreover, it is clear that TC14011, TC14012, TC14018, TC14020 and TN14003 have higher anti-HIV activity in addition to lowered cytotoxicity.

<Stability in Sera>

Figure 2:
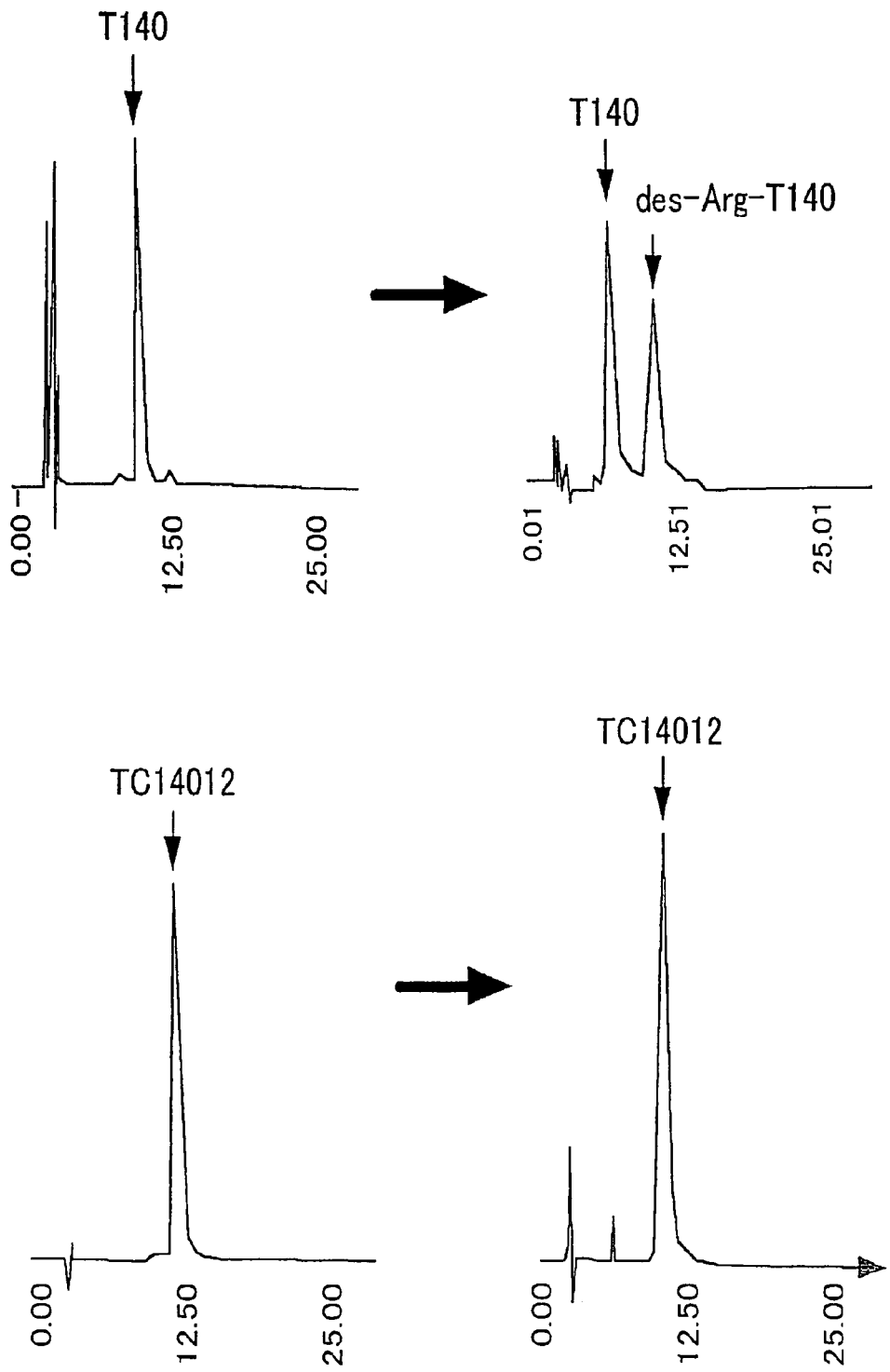
FIG. 2 is a HPLC chart showing stabilities of polypeptides TC14012 of the present invention and T140 in serum.

T140 or TC14012 was dissolved in cat serum (100 μL/100 μL Water) in an amount of 100 nmol, and maintained at 37° C. Each 8 μL of the respective samples were collected after 0 hour, 1 hour, 2 hours, 5 hours and 16 hours, and analyzed by reverse phase HPLC using 16% acetonitrile. As a result, in the case of T140, about 70% was decomposed after 16 hours, but substantially no decomposition was observed in TC14012 (FIG. 2).

This shows that the carboxyl terminus of the polypeptide according to the present invention is amidated, then stability of the polypeptide in serum is remarkably improved.

Sequence Listing Free Text

SEQ.ID.NO: 1: Designed peptide based on tachyplesin family polypeptide of horseshoe crab, 8Xaa: D-Lys, 12Xaa: L-citrulline SEQ.ID.NO: 2: Designed peptide based on tachyplesin family polypeptide of horseshoe crab, 3Xaa: L-3-(2-naphthyl)alanine, 8Xaa: D-Lys, 12Xaa: L-citrulline SEQ.ID.NO: 3: Designed peptide based on tachyplesin family polypeptide of horseshoe crab, 3Xaa: L-3-(2-naphthyl)alanine, 8Xaa: D-Lys, 12Xaa: L-citrulline SEQ.ID.NO: 4: Designed peptide based on tachyplesin family polypeptide of horseshoe crab, 3Xaa: L-3-(2-naphthyl)alanine, 8Xaa: D-Lys, 12Xaa: L-citrulline SEQ.ID.NO: 5: Designed peptide based on tachyplesin family polypeptide of horseshoe crab, 3Xaa: L-3-(2-naphthyl)alanine, 8Xaa: D-Lys, 12Xaa: L-citrulline SEQ.ID.NO: 6: Designed peptide based on tachyplesin family polypeptide of horseshoe crab, 3Xaa: L-3-(2-naphthyl)alanine, 8Xaa: D-Ala, 12Xaa: L-citrulline SEQ.ID.NO: 7: Designed peptide based on tachyplesin family polypeptide of horseshoe crab, 3Xaa: L-3-(2-naphthyl)alanine, 8Xaa: D-Lys, 12Xaa: L-citrulline SEQ.ID.NO: 8: Designed peptide based on tachyplesin family polypeptide of horseshoe crab, 3Xaa: L-3-(2-naphthyl)alanine, 8Xaa: D-Lys, 12Xaa: L-citrulline SEQ.ID.NO: 9: Designed peptide based on tachyplesin family polypeptide of horseshoe crab, 3Xaa: L-3-(2-naphthyl)alanine, 8Xaa: D-Lys, 12Xaa: L-citrulline SEQ.ID.NO: 10: Designed peptide based on tachyplesin family polypeptide of horseshoe crab, 1Xaa: L-citrulline, 3Xaa: L-3-(2-naphthyl)alanine, 8Xaa: D-Lys, 12Xaa: L-citrulline SEQ.ID.NO: 11: Designed peptide based on tachyplesin family polypeptide of horseshoe crab, 3Xaa: L-3-(2-naphthyl)alanine, 6Xaa: L-citrulline, 8Xaa: D-Lys, 12Xaa: L-citrulline SEQ.ID.NO: 12: Designed peptide based on tachyplesin family polypeptide of horseshoe crab, 3Xaa: L-3-(2-naphthyl)alanine, 7Xaa: L-citrulline, 8Xaa: D-Lys, 12Xaa: L-citrulline SEQ.ID.NO: 13: Designed peptide based on tachyplesin family polypeptide of horseshoe crab, 3Xaa: L-3-(2-naphthyl)alanine, 8Xaa: D-citrulline, 12Xaa: L-citrulline SEQ.ID.NO: 14: Designed peptide based on tachyplesin family polypeptide of horseshoe crab, 3Xaa: L-3-(2-naphthyl)alanine, 8Xaa: D-Lys, 11Xaa: L-citrulline, 12Xaa: L-citrulline SEQ.ID.NO: 15: Designed peptide based on tachyplesin family polypeptide of horseshoe crab, 3Xaa: L-3-(2-naphthyl)alanine, 6Xaa: L-citrulline, 8Xaa: D-citrulline, 12Xaa: L-citrulline SEQ.ID.NO: 16: Designed peptide based on tachyplesin family polypeptide of horseshoe crab, 1Xaa: L-citrulline, 3Xaa: L-3-(2-naphthyl)alanine, 8Xaa: D-citrulline, 12Xaa: L-citrulline SEQ.ID.NO: 17: Designed peptide based on tachyplesin family polypeptide of horseshoe crab, 3Xaa: L-3-(2-naphthyl)alanine, 8Xaa: D-citrulline, 11Xaa: L-citrulline, 12Xaa: L-citrulline

UTILIZABILITY IN INDUSTRY

According to the present invention, novel polypeptides having low cytotoxicity and high anti-HIV activity can be provided.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

SEQUENCE LISTING

```
<160> NUMBER OF SEQ ID NOS: 29

<210> SEQ ID NO 1
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (8)..(8)
<223> OTHER INFORMATION: D-Lys
<220> FEATURE:
```

-continued

<221> NAME/KEY: MOD_RES
<222> LOCATION: (12)..(12)
<223> OTHER INFORMATION: L-citrulline

<400> SEQUENCE: 1

Arg Arg Trp Cys Tyr Arg Lys Xaa Pro Tyr Arg Xaa Cys Arg
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)..(3)
<223> OTHER INFORMATION: L-3-(2-Naphthyl) alanine
<220> FEATURE:
<221> NAME/KEY: MOD_RES
<222> LOCATION: (8)..(8)
<223> OTHER INFORMATION: D-Lys
<220> FEATURE:
<221> NAME/KEY: MOD_RES
<222> LOCATION: (12)..(12)
<223> OTHER INFORMATION: L-citrulline

<400> SEQUENCE: 2

Arg Arg Xaa Cys Tyr Arg Lys Xaa Pro Tyr Arg Xaa Cys Arg
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)..(3)
<223> OTHER INFORMATION: L-3-(2-Naphthyl)alanine
<220> FEATURE:
<221> NAME/KEY: MOD_RES
<222> LOCATION: (8)..(8)
<223> OTHER INFORMATION: D-Lys
<220> FEATURE:
<221> NAME/KEY: MOD_RES
<222> LOCATION: (12)..(12)
<223> OTHER INFORMATION: L-citrulline

<400> SEQUENCE: 3

Ala Arg Xaa Cys Tyr Arg Lys Xaa Pro Tyr Arg Xaa Cys Arg
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)..(3)
<223> OTHER INFORMATION: L-3-(2-Naphthyl) alanine
<220> FEATURE:
<221> NAME/KEY: MOD_RES
<222> LOCATION: (8)..(8)
<223> OTHER INFORMATION: D-Lys
<220> FEATURE:
<221> NAME/KEY: MOD_RES
<222> LOCATION: (12)..(12)

-continued

<223> OTHER INFORMATION: L-citrulline

<400> SEQUENCE: 4

Arg Arg Xaa Cys Tyr Ala Lys Xaa Pro Tyr Arg Xaa Cys Arg
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)..(3)
<223> OTHER INFORMATION: L-3-(2-Naphthyl)alanine
<220> FEATURE:
<221> NAME/KEY: MOD_RES
<222> LOCATION: (8)..(8)
<223> OTHER INFORMATION: D-Lys
<220> FEATURE:
<221> NAME/KEY: MOD_RES
<222> LOCATION: (12)..(12)
<223> OTHER INFORMATION: L-citrulline

<400> SEQUENCE: 5

Arg Arg Xaa Cys Tyr Arg Ala Xaa Pro Tyr Arg Xaa Cys Arg
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)..(3)
<223> OTHER INFORMATION: L-3-(2-Naphthyl) alanine
<220> FEATURE:
<221> NAME/KEY: MOD_RES
<222> LOCATION: (8)..(8)
<223> OTHER INFORMATION: D-Lys
<220> FEATURE:
<221> NAME/KEY: MOD_RES
<222> LOCATION: (12)..(12)
<223> OTHER INFORMATION: L-citrulline

<400> SEQUENCE: 6

Arg Arg Xaa Cys Tyr Arg Lys Xaa Pro Tyr Arg Xaa Cys Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)..(3)
<223> OTHER INFORMATION: L-3-(2-Naphthyl) alanine
<220> FEATURE:
<221> NAME/KEY: MOD_RES
<222> LOCATION: (8)..(8)
<223> OTHER INFORMATION: D-Lys
<220> FEATURE:
<221> NAME/KEY: MOD_RES
<222> LOCATION: (12)..(12)
<223> OTHER INFORMATION: L-citrulline

```
<400> SEQUENCE: 7

Arg Arg Xaa Cys Tyr Arg Lys Xaa Ala Tyr Arg Xaa Cys Arg
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)..(3)
<223> OTHER INFORMATION: L-3-(2-Naphthyl) alanine
<220> FEATURE:
<221> NAME/KEY: MOD_RES
<222> LOCATION: (8)..(8)
<223> OTHER INFORMATION: D-Lys
<220> FEATURE:
<221> NAME/KEY: MOD_RES
<222> LOCATION: (12)..(12)
<223> OTHER INFORMATION: L-citrulline

<400> SEQUENCE: 8

Arg Arg Xaa Cys Tyr Arg Lys Xaa Pro Ala Arg Xaa Cys Arg
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)..(3)
<223> OTHER INFORMATION: L-3-(2-Naphthyl) alanine
<220> FEATURE:
<221> NAME/KEY: MOD_RES
<222> LOCATION: (8)..(8)
<223> OTHER INFORMATION: D-Lys
<220> FEATURE:
<221> NAME/KEY: MOD_RES
<222> LOCATION: (12)..(12)
<223> OTHER INFORMATION: L-citrulline

<400> SEQUENCE: 9

Arg Arg Xaa Cys Tyr Arg Lys Xaa Pro Tyr Ala Xaa Cys Arg
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (1)..(1)
<223> OTHER INFORMATION: L-citrulline
<220> FEATURE:
<221> NAME/KEY: MOD_RES
<222> LOCATION: (3)..(3)
<223> OTHER INFORMATION: L-3-(2-Naphthyl) alanine
<220> FEATURE:
<221> NAME/KEY: MOD_RES
<222> LOCATION: (8)..(8)
<223> OTHER INFORMATION: D-Lys
<220> FEATURE:
<221> NAME/KEY: MOD_RES
<222> LOCATION: (12)..(12)
```

-continued

<223> OTHER INFORMATION: L-citrulline

<400> SEQUENCE: 10

Xaa Arg Xaa Cys Tyr Arg Lys Xaa Pro Tyr Arg Xaa Cys Arg
 1               5                  10

<210> SEQ ID NO 11
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: misc_feature
<223> OTHER INFORMATION: C' Amidated peptide
<220> FEATURE:
<221> NAME/KEY: MOD_RES
<222> LOCATION: (3)..(3)
<223> OTHER INFORMATION: L-3-(2-Naphthyl) alanine
<220> FEATURE:
<221> NAME/KEY: MOD_RES
<222> LOCATION: (6)..(6)
<223> OTHER INFORMATION: L-citrulline
<220> FEATURE:
<221> NAME/KEY: MOD_RES
<222> LOCATION: (8)..(8)
<223> OTHER INFORMATION: D-Lys
<220> FEATURE:
<221> NAME/KEY: MOD_RES
<222> LOCATION: (12)..(12)
<223> OTHER INFORMATION: L-citrulline

<400> SEQUENCE: 11

Arg Arg Xaa Cys Tyr Xaa Lys Xaa Pro Tyr Arg Xaa Cys Arg
 1               5                  10

<210> SEQ ID NO 12
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)..(3)
<223> OTHER INFORMATION: L-3-(2-Naphthyl) alanine
<220> FEATURE:
<221> NAME/KEY: MOD_RES
<222> LOCATION: (7)..(7)
<223> OTHER INFORMATION: L-citrulline
<220> FEATURE:
<221> NAME/KEY: MOD_RES
<222> LOCATION: (8)..(8)
<223> OTHER INFORMATION: D-Lys
<220> FEATURE:
<221> NAME/KEY: MOD_RES
<222> LOCATION: (12)..(12)
<223> OTHER INFORMATION: L-citrulline

<400> SEQUENCE: 12

Arg Arg Xaa Cys Tyr Arg Xaa Xaa Pro Tyr Arg Xaa Cys Arg
 1               5                  10

<210> SEQ ID NO 13
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: misc_feature

```
<223> OTHER INFORMATION: C' Amidated peptide
<220> FEATURE:
<221> NAME/KEY: MOD_RES
<222> LOCATION: (3)..(3)
<223> OTHER INFORMATION: L-3-(2-Naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: L-citrulline

<400> SEQUENCE: 13

Arg Arg Xaa Cys Tyr Arg Lys Xaa Pro Tyr Arg Xaa Cys Arg
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)..(3)
<223> OTHER INFORMATION: L-3-(2-Naphthyl) alanine
<220> FEATURE:
<221> NAME/KEY: MOD_RES
<222> LOCATION: (8)..(8)
<223> OTHER INFORMATION: D-Lys
<220> FEATURE:
<221> NAME/KEY: MOD_RES
<222> LOCATION: (11)..(12)
<223> OTHER INFORMATION: L-citrulline

<400> SEQUENCE: 14

Arg Arg Xaa Cys Tyr Arg Lys Xaa Pro Tyr Xaa Xaa Cys Arg
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: misc_feature
<223> OTHER INFORMATION: C' Amidated peptide
<220> FEATURE:
<221> NAME/KEY: MOD_RES
<222> LOCATION: (3)..(3)
<223> OTHER INFORMATION: L-3-(2-Naphthyl) alanine
<220> FEATURE:
<221> NAME/KEY: MOD_RES
<222> LOCATION: (6)..(6)
<223> OTHER INFORMATION: L-citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: L-citrulline

<400> SEQUENCE: 15

Arg Arg Xaa Cys Tyr Xaa Lys Xaa Pro Tyr Arg Xaa Cys Arg
1               5                   10

<210> SEQ ID NO 16
```

```
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: misc_feature
<223> OTHER INFORMATION: C' Amidated peptide
<220> FEATURE:
<221> NAME/KEY: MOD_RES
<222> LOCATION: (1)..(1)
<223> OTHER INFORMATION: L-citrulline
<220> FEATURE:
<221> NAME/KEY: MOD_RES
<222> LOCATION: (3)..(3)
<223> OTHER INFORMATION: L-3-(2-Naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: L-citrulline

<400> SEQUENCE: 16

Xaa Arg Xaa Cys Tyr Arg Lys Xaa Pro Tyr Arg Xaa Cys Arg
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)..(3)
<223> OTHER INFORMATION: L-3-(2-Naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (11)..(12)
<223> OTHER INFORMATION: L-citrulline

<400> SEQUENCE: 17

Arg Arg Xaa Cys Tyr Arg Lys Xaa Pro Tyr Xaa Xaa Cys Arg
1               5                   10

<210> SEQ ID NO 18
<211> LENGTH: 18
<212> TYPE: PRT
<213> ORGANISM: Artificial Sequence
<220> FEATURE:
<223> OTHER INFORMATION: Formula peptide
<220> FEATURE:
<221> NAME/KEY: misc_feature
<223> OTHER INFORMATION: see specification as filed for detailed
      description of substitutions and preferred embodiments
<220> FEATURE:
<221> NAME/KEY: MOD_RES
<222> LOCATION: (1)..(1)
<223> OTHER INFORMATION: Arg, Lys, Ala, ornithine, citrulline, any
      derivative of these amino acids, or not present
<220> FEATURE:
<221> NAME/KEY: misc_feature
<222> LOCATION: (1)..(18)
<223> OTHER INFORMATION: this sequence is structured with the proviso
      that either of the amino acid residues at positions 1, 6, 7, 14,
      15 and 18 is Ala or citrulline or that the single amino acid that
      may be present at position 8 is D-citrulline, citrulline, D-Ala or
```

```
            Ala
<220> FEATURE:
<221> NAME/KEY: MOD_RES
<222> LOCATION: (3)..(3)
<223> OTHER INFORMATION: Any aromatic amino acid
<220> FEATURE:
<221> NAME/KEY: DISULFID
<222> LOCATION: (4)..(17)
<223> OTHER INFORMATION: A disulfide bond may be formed between the Cys
      residue at position 4 and 17
<220> FEATURE:
<221> NAME/KEY: MOD_RES
<222> LOCATION: (6)..(7)
<223> OTHER INFORMATION: Arg, Lys, Ala, ornithine or citrulline
<220> FEATURE:
<221> NAME/KEY: MOD_RES
<222> LOCATION: (8)..(8)
<223> OTHER INFORMATION: Ala, Val, Leu, IIe, Ser, Cys or Met
<220> FEATURE:
<221> NAME/KEY: DISULFID
<222> LOCATION: (8)..(13)
<223> OTHER INFORMATION: When positions 8 and 13 are Cys, they may form
      a disulfide bond
<220> FEATURE:
<221> NAME/KEY: misc_feature
<222> LOCATION: (8)..(13)
<223> OTHER INFORMATION: according to the specification as filed, this
      range may be encompassed by a single residue containing a
      D-citrulline, D-Ala, citrulline or Ala
<220> FEATURE:
<221> NAME/KEY: misc_feature
<222> LOCATION: (8)..(13)
<223> OTHER INFORMATION: According to the specification as filed, this
      range may be encompassed by a single residue selected from a group
      consisting of: D-ornithyl-proline, prolyl-D-ornithine,
      D-Iysyl-proline, prolyl-D-lysine, D-arginyl-proline and
      prolyl-D-arginine
<220> FEATURE:
<221> NAME/KEY: misc_feature
<222> LOCATION: (8)..(13)
<223> OTHER INFORMATION: According to the specification as filed, this
      range may be encompassed by a single residue selected from a group
      consisting of: D-citrullyl-proline, D-citrullyl-alanine,
      D-alanine-citrulline, prolyl-D-citrulline glycyl-ornithine and
<220> FEATURE:
<221> NAME/KEY: misc_feature
<222> LOCATION: (8)..(13)
<223> OTHER INFORMATION: According to the specification as filed, this
      range may be encompassed by a single residue selected from a group
      consisting of: glycyl-lysine, lysyl-glycine, glycyl-arginine and
      arginyl-glycine
<220> FEATURE:
<221> NAME/KEY: misc_feature
<222> LOCATION: (8)..(13)
<223> OTHER INFORMATION: According to the specification as filed, this
      range may be encompassed by a single residue selected from a group
      consisting of: glycyl-citrulline, citrullyl-glycine D-alanyl-
      proline and D-lysyl-alanine.
<220> FEATURE:
<221> NAME/KEY: MOD_RES
<222> LOCATION: (9)..(9)
<223> OTHER INFORMATION: Any aromatic amino acid
<220> FEATURE:
<221> NAME/KEY: MOD_RES
<222> LOCATION: (10)..(10)
<223> OTHER INFORMATION: Arg, Lys, Ala, ornithine or citrulline
<220> FEATURE:
<221> NAME/KEY: MOD_RES
<222> LOCATION: (12)..(12)
<223> OTHER INFORMATION: Tyr, Phe, Trp, Ala, Val, Leu, lIe, Ser, Cys or
      Met; see specification as filed for detailed description of
      substitutions and preferred embodiments
<220> FEATURE:
<221> NAME/KEY: MOD_RES
<222> LOCATION: (13)..(13)
<223> OTHER INFORMATION: Ala, Val, Leu, lIe, Ser, Cys or Met
<220> FEATURE:
<221> NAME/KEY: MOD_RES
<222> LOCATION: (14)..(14)
<223> OTHER INFORMATION: Tyr, Phe, Ala, naphthyl-alanine or citrulline
```

```
<220> FEATURE:
<221> NAME/KEY: MOD_RES
<222> LOCATION: (15)..(15)
<223> OTHER INFORMATION: Arg, Lys, Ala, ornithine or citrulline
<220> FEATURE:
<221> NAME/KEY: MOD_RES
<222> LOCATION: (16)..(16)
<223> OTHER INFORMATION: citrulline
<220> FEATURE:
<221> NAME/KEY: MOD_RES
<222> LOCATION: (18)..(18)
<223> OTHER INFORMATION: Lys or Arg; a carboxyl group may be amidated

<400> SEQUENCE: 18

Xaa Arg Xaa Cys Tyr Xaa Xaa Xaa Xaa Xaa Gly Xaa Xaa Xaa Xaa Xaa
1               5                   10                  15

Cys Xaa

<210> SEQ ID NO 19
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Citrulline
<220> FEATURE:
<221> NAME/KEY: misc_feature
<222> LOCATION: (3)..(3)
<223> OTHER INFORMATION: Naphthylalanine
<220> FEATURE:
<221> NAME/KEY: misc_feature
<222> LOCATION: (6)..(6)
<223> OTHER INFORMATION: Citrulline
<220> FEATURE:
<221> NAME/KEY: misc_feature
<222> LOCATION: (8)..(8)
<223> OTHER INFORMATION: D stereo isomer
<220> FEATURE:
<221> NAME/KEY: misc_feature
<222> LOCATION: (12)..(12)
<223> OTHER INFORMATION: L-Citrulline

<400> SEQUENCE: 19

Xaa Arg Xaa Cys Tyr Xaa Lys Lys Pro Tyr Arg Xaa Cys Arg
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Naphthylalanine
<220> FEATURE:
<221> NAME/KEY: misc_feature
<222> LOCATION: (6)..(6)
<223> OTHER INFORMATION: L-citrulline
<220> FEATURE:
<221> NAME/KEY: misc_feature
<222> LOCATION: (8)..(8)
<223> OTHER INFORMATION: D stereo isomer
<220> FEATURE:
<221> NAME/KEY: misc_feature
<222> LOCATION: (12)..(12)
<223> OTHER INFORMATION: L-citrulline

<400> SEQUENCE: 20

Arg Arg Xaa Cys Tyr Xaa Lys Lys Pro Tyr Arg Xaa Cys Arg
```

<210> SEQ ID NO 21
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Naphthylalanine
<220> FEATURE:
<221> NAME/KEY: misc_feature
<222> LOCATION: (8)..(8)
<223> OTHER INFORMATION: D-citrulline
<220> FEATURE:
<221> NAME/KEY: misc_feature
<222> LOCATION: (12)..(12)
<223> OTHER INFORMATION: L-citrulline

<400> SEQUENCE: 21

Arg Arg Xaa Cys Tyr Arg Lys Xaa Pro Tyr Arg Xaa Cys Arg
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Naphthylalanine
<220> FEATURE:
<221> NAME/KEY: misc_feature
<222> LOCATION: (6)..(6)
<223> OTHER INFORMATION: L-Citrulline
<220> FEATURE:
<221> NAME/KEY: misc_feature
<222> LOCATION: (8)..(8)
<223> OTHER INFORMATION: D-Citrulline
<220> FEATURE:
<221> NAME/KEY: misc_feature
<222> LOCATION: (12)..(12)
<223> OTHER INFORMATION: L-Citrulline

<400> SEQUENCE: 22

Arg Arg Xaa Cys Tyr Xaa Lys Xaa Pro Tyr Arg Xaa Cys Arg
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Arginine, Alanine or Citrulline residue
<220> FEATURE:
<221> NAME/KEY: misc_feature
<222> LOCATION: (3)..(3)
<223> OTHER INFORMATION: tryptophane or naphthylalanine residue
<220> FEATURE:
<221> NAME/KEY: misc_feature
<222> LOCATION: (6)..(12)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: alanine or citrulline residue
<220> FEATURE:

```
<221> NAME/KEY: misc_feature
<222> LOCATION: (7)..(7)
<223> OTHER INFORMATION: lysine, alanine or citrulline residue
<220> FEATURE:
<221> NAME/KEY: misc_feature
<222> LOCATION: (8)..(9)
<223> OTHER INFORMATION: O-lysyl proline, O-alanyl proline, O-lysyl
      alanine or D-citrullyl proline residue
<220> FEATURE:
<221> NAME/KEY: misc_feature
<222> LOCATION: (10)..(10)
<223> OTHER INFORMATION: tyrosine or alanine residue
<220> FEATURE:
<221> NAME/KEY: misc_feature
<222> LOCATION: (11)..(11)
<223> OTHER INFORMATION: arginine, alanine or citrulline residue
<220> FEATURE:
<221> NAME/KEY: misc_feature
<222> LOCATION: (12)..(12)
<223> OTHER INFORMATION: citrulline

<400> SEQUENCE: 23

Xaa Arg Xaa Cys Tyr Xaa Xaa Xaa Xaa Xaa Xaa Xaa Cys Arg
1               5                   10

<210> SEQ ID NO 24
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: see specification as filed for detailed
      description of substitutions and preferred embodiments
<220> FEATURE:
<221> NAME/KEY: MOD_RES
<222> LOCATION: (1)..(1)
<223> OTHER INFORMATION: Arg, Lys, Ala, ornithine, citrulline, any
      derivative of these amino acids, or not present
<220> FEATURE:
<221> NAME/KEY: misc_feature
<222> LOCATION: (1)..(18)
<223> OTHER INFORMATION: this sequence is structured with the proviso
      that either of the amino acid residues at positions 1, 6 and 15 is
      Ala or citrulline or that the single amino acid that may be
      present at position 8 is D-citrulline, citrulline, D-Ala or Ala
<220> FEATURE:
<221> NAME/KEY: MOD_RES
<222> LOCATION: (3)..(3)
<223> OTHER INFORMATION: naphthylalanine
<220> FEATURE:
<221> NAME/KEY: DISULFID
<222> LOCATION: (4)..(12)
<223> OTHER INFORMATION: when position 12 is Cys, a disulfide bond may
      be formed with the Cys at position 4
<220> FEATURE:
<221> NAME/KEY: MOD_RES
<222> LOCATION: (6)..(6)
<223> OTHER INFORMATION: Arg, Lys, Ala, ornithine or citrulline
<220> FEATURE:
<221> NAME/KEY: MOD_RES
<222> LOCATION: (8)..(8)
<223> OTHER INFORMATION: Ala, Val, Leu, Ile, Ser, Cys or Met
<220> FEATURE:
<221> NAME/KEY: DISULFID
<222> LOCATION: (8)..(13)
<223> OTHER INFORMATION: when positions 8 and 13 are Cys, they may form
      a disulfide bond
<220> FEATURE:
<221> NAME/KEY: misc_feature
<222> LOCATION: (8)..(13)
<223> OTHER INFORMATION: according to the specification as filed, this
      range may be encompassed by a single residue containing a
      D-citrulline, D-Ala, citrulline or Ala
<220> FEATURE:
<221> NAME/KEY: MOD_RES
<222> LOCATION: (9)..(9)
```

```
<223> OTHER INFORMATION: Any aromatic amino acid
<220> FEATURE:
<221> NAME/KEY: MOD_RES
<222> LOCATION: (10)..(10)
<223> OTHER INFORMATION: Arg, Lys, Ala, ornithine or citrulline
<220> FEATURE:
<221> NAME/KEY: MOD_RES
<222> LOCATION: (12)..(12)
<223> OTHER INFORMATION: Tyr, Phe, Trp, Ala, Val, Leu, lIe, Ser, Cys or
      Met; see specification as filed for detailed description of
      substitutions and preferred embodiments
<220> FEATURE:
<221> NAME/KEY: MOD_RES
<222> LOCATION: (13)..(13)
<223> OTHER INFORMATION: Ala, Val, Leu, lIe, Ser, Cys or Met
<220> FEATURE:
<221> NAME/KEY: MOD_RES
<222> LOCATION: (15)..(15)
<223> OTHER INFORMATION: Arg, Lys, Ala, ornithine or citrulline
<220> FEATURE:
<221> NAME/KEY: MOD_RES
<222> LOCATION: (16)..(16)
<223> OTHER INFORMATION: Citrulline

<400> SEQUENCE: 24

Xaa Arg Xaa Cys Tyr Xaa Lys Xaa Xaa Xaa Gly Xaa Xaa Tyr Xaa Xaa
1               5                   10                  15

Cys Arg

<210> SEQ ID NO 25
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: arginine, lysine, ornithine, citrulline or
      alanine residue or a residue of N-a-substituted derivative of
      these amino acids
<220> FEATURE:
<221> NAME/KEY: misc_feature
<222> LOCATION: (3)..(3)
<223> OTHER INFORMATION: naphthyl alanine
<220> FEATURE:
<221> NAME/KEY: misc_feature
<222> LOCATION: (8)..(9)
<223> OTHER INFORMATION: D-lysyl-proline
<220> FEATURE:
<221> NAME/KEY: misc_feature
<222> LOCATION: (12)..(12)
<223> OTHER INFORMATION: citrulline

<400> SEQUENCE: 25

Xaa Arg Xaa Cys Tyr Arg Lys Xaa Xaa Tyr Arg Xaa Cys Arg
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: arginine, lysine, ornithine, citrulline or
      alanine residue or a residue of N-a-substituted derivative of
      these amino acids
<220> FEATURE:
<221> NAME/KEY: misc_feature
<222> LOCATION: (3)..(3)
<223> OTHER INFORMATION: naphthyl alanine
<220> FEATURE:
```

-continued

```
<221> NAME/KEY: misc_feature
<222> LOCATION: (8)..(9)
<223> OTHER INFORMATION: D-citrullyl proline
<220> FEATURE:
<221> NAME/KEY: misc_feature
<222> LOCATION: (11)..(11)
<223> OTHER INFORMATION: arg, ala or citrulline residue
<220> FEATURE:
<221> NAME/KEY: misc_feature
<222> LOCATION: (12)..(12)
<223> OTHER INFORMATION: citrulline

<400> SEQUENCE: 26

Xaa Arg Xaa Cys Tyr Arg Lys Xaa Xaa Tyr Xaa Xaa Cys Arg
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: arginine, lysine, ornithine, citrulline or
      alanine residue or a residue of N-a-substituted derivative of
      these amino acids
<220> FEATURE:
<221> NAME/KEY: misc_feature
<222> LOCATION: (3)..(3)
<223> OTHER INFORMATION: naphthyl alanine
<220> FEATURE:
<221> NAME/KEY: misc_feature
<222> LOCATION: (6)..(6)
<223> OTHER INFORMATION: citrulline
<220> FEATURE:
<221> NAME/KEY: misc_feature
<222> LOCATION: (8)..(9)
<223> OTHER INFORMATION: D-citrullyl proline
<220> FEATURE:
<221> NAME/KEY: misc_feature
<222> LOCATION: (11)..(11)
<223> OTHER INFORMATION: arg, ala or citrulline residue
<220> FEATURE:
<221> NAME/KEY: misc_feature
<222> LOCATION: (12)..(12)
<223> OTHER INFORMATION: citrulline

<400> SEQUENCE: 27

Xaa Arg Xaa Cys Tyr Xaa Lys Xaa Xaa Tyr Xaa Xaa Cys Arg
1               5                   10

<210> SEQ ID NO 28
<211> LENGTH: 18
<212> TYPE: PRT
<213> ORGANISM: Artificial Sequence
<220> FEATURE:
<223> OTHER INFORMATION: Formula peptide
<220> FEATURE:
<221> NAME/KEY: misc_feature
<223> OTHER INFORMATION: see specification as filed for detailed
      description of substitutions and preferred embodiments
<220> FEATURE:
<221> NAME/KEY: MOD_RES
<222> LOCATION: (1)..(1)
<223> OTHER INFORMATION: Arg, Lys, Ala, ornithine, citrulline, any
      derivative of these amino acids, or not present
<220> FEATURE:
<221> NAME/KEY: misc_feature
<222> LOCATION: (1)..(18)
<223> OTHER INFORMATION: this sequence is structured with the proviso
      that either of the amino acid residues at positions I, 6, 7, 14,
      15 and is Ala or citrulline or that the single amino acid that may
      be present at position 8 is D-citrulline, citrulline, D-Ala or Ala
<220> FEATURE:
```

```
<221> NAME/KEY: MOD_RES
<222> LOCATION: (3)..(3)
<223> OTHER INFORMATION: Any aromatic amino acid
<220> FEATURE:
<221> NAME/KEY: DISULFID
<222> LOCATION: (4)..(12)
<223> OTHER INFORMATION: when position 12 is Cys, a disulfide bond may
      be formed with the Cys at position 4
<220> FEATURE:
<221> NAME/KEY: MOD_RES
<222> LOCATION: (6)..(7)
<223> OTHER INFORMATION: Arg, Lys, Ala, ornithine or citrulline
<220> FEATURE:
<221> NAME/KEY: MOD_RES
<222> LOCATION: (8)..(8)
<223> OTHER INFORMATION: Ala, Val, Leu, lIe, Ser, Cys or Met
<220> FEATURE:
<221> NAME/KEY: DISULFID
<222> LOCATION: (8)..(13)
<223> OTHER INFORMATION: when positions 8 and 13 are Cys, they may form
      a disulfide bond
<220> FEATURE:
<221> NAME/KEY: misc_feature
<222> LOCATION: (8)..(13)
<223> OTHER INFORMATION: According to the specification as filed, this
      range may be encompassed by a single residue containing a
      D-citrulline, D-Ala, citrulline or Ala
<220> FEATURE:
<221> NAME/KEY: MOD_RES
<222> LOCATION: (9)..(9)
<223> OTHER INFORMATION: Any aromatic amino acid
<220> FEATURE:
<221> NAME/KEY: MOD_RES
<222> LOCATION: (10)..(10)
<223> OTHER INFORMATION: Arg, Lys, Ala, ornithine or citrulline
<220> FEATURE:
<221> NAME/KEY: MOD_RES
<222> LOCATION: (12)..(12)
<223> OTHER INFORMATION: Tyr, Phe, Trp, Ala, Val, Leu, lIe, Ser, Cys or
      Met; see specification as filed for detailed description of
      substitutions and preferred embodiments
<220> FEATURE:
<221> NAME/KEY: MOD_RES
<222> LOCATION: (13)..(13)
<223> OTHER INFORMATION: Ala, Val, Leu, lIe, Ser, eys or Met
<220> FEATURE:
<221> NAME/KEY: MOD_RES
<222> LOCATION: (14)..(14)
<223> OTHER INFORMATION: Tyr, Phe, Ala, naphthylalanine or citrulline
<220> FEATURE:
<221> NAME/KEY: MOD_RES
<222> LOCATION: (15)..(15)
<223> OTHER INFORMATION: Arg, Lys, Ala, ornithine or citrulline
<220> FEATURE:
<221> NAME/KEY: MOD_RES
<222> LOCATION: (16)..(16)
<223> OTHER INFORMATION: citrulline
<220> FEATURE:
<221> NAME/KEY: MOD_RES
<222> LOCATION: (18)..(18)
<223> OTHER INFORMATION: Lys or Arg; a carboxyl is amidated

<400> SEQUENCE: 28

Xaa Arg Xaa Cys Tyr Xaa Xaa Xaa Xaa Xaa Gly Xaa Xaa Xaa Xaa Xaa
1               5                   10                  15

Cys Xaa

<210> SEQ ID NO 29
<211> LENGTH: 6
<212> TYPE: PRT
<213> ORGANISM: Artificial Sequence
<220> FEATURE:
<223> OTHER INFORMATION: Formula peptide
<220> FEATURE:
<221> NAME/KEY: misc_feature
<223> OTHER INFORMATION: see specification as filed for detailed
      description of substitutions and preferred embodiments
```

```
<220> FEATURE:
<221> NAME/KEY: misc_feature
<222> LOCATION: (1)..(1)
<223> OTHER INFORMATION: Ala, Val, Leu, Ile, Ser, Cys or Met residue
<220> FEATURE:
<221> NAME/KEY: DISULFID
<222> LOCATION: (1)..(6)
<223> OTHER INFORMATION: when positions 1 and 6 are Cys, they may form a
      disulfide bond
<220> FEATURE:
<221> NAME/KEY: misc_feature
<222> LOCATION: (2)..(2)
<223> OTHER INFORMATION: Any aromatic amino acid
<220> FEATURE:
<221> NAME/KEY: misc_feature
<222> LOCATION: (3)..(3)
<223> OTHER INFORMATION: Arg, Lys, Ala, ornithine or citrulline
<220> FEATURE:
<221> NAME/KEY: misc_feature
<222> LOCATION: (5)..(5)
<223> OTHER INFORMATION: Tyr, Phe, Trp, Ala, Val, Leu, Ile, Ser, Cys or
      Met;
<220> FEATURE:
<221> NAME/KEY: misc_feature
<222> LOCATION: (6)..(6)
<223> OTHER INFORMATION: Ala, Val, Leu, Ile, Ser, Cys or Met residue

<400> SEQUENCE: 29

Xaa Xaa Xaa Gly Xaa Xaa
1               5
```

The invention claimed is:

1. A method for inhibiting HIV infection in a subject in need thereof, wherein said HIV is of a strain which involves CXCR4 in the infection, comprising contacting cells of the subject with an effective amount of a polypeptide having an amino acid sequence as set forth in any one of ID NOs: 3-16 and 20-22.

2. The method of claim 1, wherein the cells are selected from peripheral blood mononuclear cells and CD4+ T cells.

3. The method of claim 1, wherein the cells are contacted with the polypeptide ex vivo.

4. The method of claim 1, wherein the cells are contacted with the polypeptide in vivo.

5. The method of claim 4, wherein the polypeptide is administered to said subject in the form of a pharmaceutical composition further comprising a physiologically acceptable carrier.

6. The method of claim 1, wherein the polypeptide is conjugated to a reverse transcriptase inhibitor, an HIV protease inhibitor or an in-vivo half-time elongating substance.

7. A method for treating a subject in need of an anti-HIV therapy, wherein the subject is infected with an HIV-1 strain, which involves CXCR4 in the infection, the method comprising contacting cells of the subject with an effective amount of a polypeptide having an amino acid sequence as set forth in any one of SEQ ID NOs: 3-16 and 20-22.

8. The method of claim 7, wherein the cells are selected from peripheral blood mononuclear cells and CD4+ T cells.

9. The method of claim 7, wherein the cells are contacted with the polypeptide ex vivo.

10. The method of claim 7, wherein the cells are contacted with the polypeptide in vivo.

11. The method of claim 10, wherein the polypeptide is administered to said subject in the form of a pharmaceutical composition further comprising a physiologically acceptable carrier.

12. The method of claim 7, wherein the polypeptide is conjugated to a reverse transcriptase inhibitor, an HIV protease inhibitor or an in-vivo half-time elongating substance.

13. A method for preventing or reducing HIV-induced cell death, wherein said HIV is of a strain which involves CXCR4 in the infection, the method comprising contacting cells of a subject in need thereof with an effective amount of a polypeptide having an amino acid sequence as set forth in any one of SEQ ID NOs: 3-16 and 20-22.

14. The method of claim 13, wherein the cells are selected from peripheral blood mononuclear cells and CD4+ T cells.

15. The method of claim 13, wherein the cells are contacted with the polypeptide ex vivo.

16. The method of claim 13, wherein the cells are contacted with the polypeptide in vivo.

17. The method of claim 16, wherein the polypeptide is administered to said subject in the form of a pharmaceutical composition further comprising a physiologically acceptable carrier.

18. The method of claim 13, wherein the polypeptide is conjugated to a reverse transcriptase inhibitor, an HIV protease inhibitor or an in-vivo half-time elongating substance.

19. The method of claim 1, wherein said HIV strain is HIV-1 IIIb.

20. The method of claim 7, wherein said HIV strain is HIV-1 IIIb.

21. The method of claim 13, wherein said HIV strain is HIV-1 IIIb.

* * * * *